(12) United States Patent
Nakashima et al.

(10) Patent No.: US 10,668,134 B2
(45) Date of Patent: Jun. 2, 2020

(54) DENTAL PRETREATMENT MATERIAL AND DENTAL TISSUE REGENERATION KIT

(71) Applicant: National Center for Geriatrics and Gerontology, Aichi (JP)

(72) Inventors: Misako Nakashima, Aichi (JP); Koichiro Iohara, Aichi (JP); Hideto Watanabe, Aichi (JP)

(73) Assignee: NATIONAL CENTER FOR GERIATRICS AND GERONTOLOGY, Aichi (JP)

( * ) Notice: Subject to any disclaimer, the term of this patent is extended or adjusted under 35 U.S.C. 154(b) by 0 days.

(21) Appl. No.: 16/086,993

(22) PCT Filed: Mar. 31, 2017

(86) PCT No.: PCT/JP2017/013572
§ 371 (c)(1),
(2) Date: Dec. 4, 2018

(87) PCT Pub. No.: WO2017/170996
PCT Pub. Date: Oct. 5, 2017

(65) Prior Publication Data
US 2019/0282675 A1     Sep. 19, 2019

(30) Foreign Application Priority Data

Mar. 31, 2016 (JP) .................... 2016-072306

(51) Int. Cl.
| | | |
|---|---|---|
| *A61K 38/48* | (2006.01) | |
| *A61P 1/02* | (2006.01) | |
| *A61K 9/51* | (2006.01) | |
| *A61L 27/38* | (2006.01) | |
| *A61L 27/54* | (2006.01) | |
| *A61L 27/50* | (2006.01) | |
| *A61K 6/00* | (2020.01) | |
| *A61K 6/80* | (2020.01) | |

(52) U.S. Cl.
CPC ............ *A61K 38/4826* (2013.01); *A61K 6/00* (2013.01); *A61K 6/80* (2020.01); *A61K 9/51* (2013.01); *A61K 38/48* (2013.01); *A61L 27/3804* (2013.01); *A61L 27/3865* (2013.01); *A61L 27/50* (2013.01); *A61L 27/54* (2013.01); *A61P 1/02* (2018.01); *C12Y 304/21004* (2013.01)

(58) Field of Classification Search
CPC .. A61L 27/54; A61L 27/3865; A61L 27/3804; A61K 38/4826; A61K 6/02; A61K 9/51; C12Y 304/21004; A61P 1/02
See application file for complete search history.

(56) References Cited

U.S. PATENT DOCUMENTS

| | | |
|---|---|---|
| 2008/0280252 A1 | 11/2008 | Riva |
| 2011/0020310 A1 | 1/2011 | Nakashima et al. |
| 2012/0164604 A1 | 6/2012 | Nakashima et al. |
| 2014/0099605 A1 | 4/2014 | Nakashima et al. |

FOREIGN PATENT DOCUMENTS

| | | | |
|---|---|---|---|
| EP | 1754464 A1 | 2/2007 | |
| EP | 2263706 A1 | 12/2010 | |
| JP | S58-148825 A | 9/1983 | |
| JP | S58-148828 A | 9/1983 | |
| JP | H10-139684 A | 5/1998 | |
| JP | 2009-513227 A | 4/2009 | |
| JP | 2011-078752 A | 4/2011 | |
| JP | 2014-168714 A | 9/2014 | |
| JP | 5621105 B2 | 11/2014 | |
| JP | 5748194 B2 | 7/2015 | |
| WO | WO-2010115836 A1 * | 10/2010 | ............. A61K 31/56 |

OTHER PUBLICATIONS

Prescott et al. In-vivo Generation of Dental Pulp-Like Tissue Using Human Pulpal Stem Cells, a Collagen Scaffold and Dentin Matrix Protein 1 Following Subcutaneous Transplantation in Mice. J Endod. (2008), 34(4), 14 page reprint. (Year: 2008).*
Andersson, O., et al., "Growth differentiation factor 11 signals trough the transforming growth factor-β receptor ALK5 to regionalize the anterior-posterior axis", *EMBO Reports*, 7(8): 831-7, 2006.
Fujita, M., et al., Pulp Regeneration after Complete Disinfection for the Root Canal System by Enhanced Delivery of Medicaments using Ultrasound with Nanobubbles in a Canine Periapical Disease Model, *The Japanese Journal of Conservative Dentistry*, Apr. 2014, pp. 170-179, vol. 57, No. 2, Japan.
Iohara, K., et al., "A novel combinatorial therapy with pulp stem cells and granulocyte colony-stimulating factor for total pulp regeneration", *Stem Cells Transl. Med.* 2(7): 521-533, 2013.
Iohara, K., et al., "Age-dependent decline in dental pulp regeneration after pulpectomy in dogs", *Exp. Gerontol*, 52:39-45, 2014.
Katsimpardi, L., et al., "Vascular and neurogenic rejuvenation of the aging mouse brain by young systemic factors", *Science*, 344(6184):630-634, 2014.
Kitaura, M., et al., "Molecular cloning of human eotaxin, an eosinophil-selective CC chemokine, and identification of a specific eosinophil eotaxin receptor, CC chemokine receptor 3", *J Biol Chem*, 271(13): 7725-30, 1996.

(Continued)

*Primary Examiner* — Sean C. Barron
(74) *Attorney, Agent, or Firm* — Alston & Bird LLP

(57) ABSTRACT

Provided is a dental pretreatment material for dental tissue regeneration by use of dental pulp stem cells, particularly a dental pretreatment material effectively enabling dental tissue regeneration even by use of dental pulp stem cells of middle-aged or older individuals. The dental pretreatment material is characterized by comprising a serine protease, specifically trypsin. The dental pretreatment material comprising trypsin is used as an injection into a root canal before a root canal filling material comprising dental pulp stem cells and an extracellular matrix is inserted into the root canal as an attempt to regenerate a dental pulp and a dentin. The root canal filling material includes an ALK5 inhibitor, a CCR3 antagonist, or a CCL11 neutralizing antibody.

1 Claim, 17 Drawing Sheets

Specification includes a Sequence Listing.

(56) References Cited

OTHER PUBLICATIONS

Loffredo, F.S., et al., "Growth differentiation factor 11 is a circulating factor that reverses age-related cardiac hypertrophy", *Cell*, 153(4):828-839, 2013.

Nakashima, M., et al., "Expression of growth/differentiation factor 11, a new member of the BMP/TGF beta superfamily during mouse embryogenesis", *Mech Dev.*, 80(2):185-9, 1999.

Nakashima, M., et al., "Induction of dental pulp stem cell differentiation into odontoblasts by electroporation-mediated gene delivery of growth/differentiation factor 11 (Gdf11)", *Gene Therapy*, 9(12):814-8, 2002.

Noguchi, Y., et al., "Clinical Studies on the Enzyme Trypsin", The Japanese Journal of Dermatology and Venereology, 1954, 64, 497-506, Japan.

Sinha, M., et al., "Restoring dysfunction GDF11 levels reverses age-related dysfunction in mouse skeletal muscle", *Science*, 344(6184):649-52, 2014.

Villeda, S.A., et al., "The ageing systemic milieu negatively regulates neurogenesis and cognitive function", *Nature*, 477(7362):90-94, 2011.

International Searching Authority (ISA), International Search Report (ISR) and Written Opinion for International Application No. PCT/JP2017/013572, dated May 16, 2016, 10 pages, Japan Patent Office, JP.

International Preliminary Examining Authority, International Preliminary Report on Patentability Chapter I (English translation of ISA's Written Opinion) for International Application No. PCT/JP2017/013572, dated Oct. 2, 2018, 12 pages, The International Bureau of WIPO.

European Patent Office, Extended European Search Report for European Patent Application No. 17775527.9, dated Sep. 13, 2019, (13 pages), Germany.

Goldberg, Michael et al. "Inflammatory and Immunological Aspects of Dental Pulp Air," Pharmacological Research, vol. 58, No. 2, Aug. 1, 2008, pp. 137-147, Academic Press, London, Great Britain. DOI: 10.1016/j.phrs.2008.05.013.

Masanori, Fujita, et al. "Pulp Regeneration After Complete Disinfection of the Root Canal System by Enhanced Delivery of Medicaments Using Ultrasound With Nanobubbles in a Canine Periapical Disease Model," Nihon Shika Hozongaku Xasshi, The Japanese Journal of Conservative Dentistry, vol. 57, No. 2, Jan. 1, 2004, pp. 170-179. DOI: 10.11471/shikahozon.57.170.

Sharma, Sarang et al. "Regeneration of Tooth Pulp and Dentin: Trends and Advances," Annals of Neurosciences, vol. 17, No. 1, Jan. 2010, pp. 31-43.

Lin, Po-Shuen et al. "Transforming Grown Factor β1 Down-Regulates Runx-2 and Alkaline Phosphatase Activity of Human Dental Pulp Cells Via ALK5/2mad2/3 Signaling," Oral Surgery, Oral Medicine, Oral Pathology, Oral Radiology and Endodontics, vol. 111 No. 3, Sep. 29, 2010, pp. 394-400, Mosby-Year Book, St. Louis, Missouri. DOI: 10.1016/J.TRIPLEO.2010.09.079.

\* cited by examiner

A WITHOUT TRYPSIN
B 0.05% TRYPSIN
C 0.5% TRYPSIN

TREATED ONLY WITH TRYPSIN,
WITHOUT CELL
TRANSPLANTATION

```
                        SEQUENCE LISTING

<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
ggacttcgag caagagatgg                                               20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
agcactgtgt tggcgtacag                                               20

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
gaaggtccct cagacatccc c                                             21

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
ccctgtagga ccttcggtga c                                             21

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
ttctgtggct gctgctcata g                                             21

<210> SEQ ID NO 6
```

```
<211> LENGTH: 20
<212> TYPE: DNA
<213> ORGANISM: Artificial Sequence
<220> FEATURE:
<223> OTHER INFORMATION: primer

<400> SEQUENCE: 6
gctctctagt cgctgaaggg                                                 20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
ctgtactccc tggtgttcac tg                                              22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
ggttgagcag gtagatgttg g                                               21

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
caagtcgcag atcttgagca                                                 20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
cacttgcttg aagtcgatgc                                                 20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ttctgtggct gctgctcata g                                               21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
```
gctctctagt cgctgaaggg                                              20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
ctgtactccc tggtgttcac tg                                           22

<210> SEQ ID NO 14
<211> LENGTH: 21
<212> TYPE: DNA
<213> ORGANISM: Artificial Sequence
<220> FEATURE:
<223> OTHER INFORMATION: primer

<400> SEQUENCE: 14
ggttgagcag gtagatgttg g                                            21

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
gaaggtccct cagacatccc c                                            21

<210> SEQ ID NO 16
<211> LENGTH: 21
<212> TYPE: DNA
<213> ORGANISM: Artificial Sequence
<220> FEATURE:
<223> OTHER INFORMATION: primer

<400> SEQUENCE: 16
ccctgtagga ccttcggtga c                                            21

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aggccttgga actcaaggat                                              20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ccctttttgg acttcaggtg                                              20

<210> SEQ ID NO 19
<211> LENGTH: 20
<212> TYPE: DNA

```
<213> ORGANISM: Artificial Sequence
<220> FEATURE:
<223> OTHER INFORMATION: primer

<400> SEQUENCE: 19
ccaggagccc agctatgaac                                                20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
cccagggaga aggcaactg                                                 19

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
ggccctaaac agatgaagtg ct                                             22

<210> SEQ ID NO 22
<211> LENGTH: 16
<212> TYPE: DNA
<213> ORGANISM: Artificial Sequence
<220> FEATURE:
<223> OTHER INFORMATION: primer

<400> SEQUENCE: 22
tgccgccatc cagagg                                                    16

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ttggcagcct tcctgatttc                                                20

<210> SEQ ID NO 24
<211> LENGTH: 16
<212> TYPE: DNA
<213> ORGANISM: Artificial Sequence
<220> FEATURE:
<223> OTHER INFORMATION: primer

<400> SEQUENCE: 24
tgccgccatc cagagg                                                    16

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
accaggccgt gatctctatg                                                20
```

<210> SEQ ID NO 26
<211> LENGTH: 19
<212> TYPE: DNA
<213> ORGANISM: Artificial Sequence
<220> FEATURE:
<223> OTHER INFORMATION: primer

<400> SEQUENCE: 26
tccctttgtc cctggtctc                                                19

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
gaaggtccct cagacatccc c                                             21

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
ccctgtagga ccttcggtga c                                             21

<210> SEQ ID NO 29
<211> LENGTH: 20
<212> TYPE: DNA
<213> ORGANISM: Artificial Sequence
<220> FEATURE:
<223> OTHER INFORMATION: primer

<400> SEQUENCE: 29
aaacatccga ggacaaggtg                                               20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
cgtgtacaag tctgcgtcct                                               20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
atacaggcgg aaccacactc                                               20

<210> SEQ ID NO 32
<211> LENGTH: 19
<212> TYPE: DNA
<213> ORGANISM: Artificial Sequence
<220> FEATURE:

```
<223> OTHER INFORMATION: primer

<400> SEQUENCE: 32
gcctggggtc cacagtaat                                                  19

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gccccagtca cctgctgtta                                                 20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tccaggtggt ccatggaatc                                                 20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
tggtggtgat gggcgtatct                                                 20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
ctggccatca ctgctcaaag                                                 20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
cctcaggaag cttgaacctg                                                 20

<210> SEQ ID NO 38
<211> LENGTH: 20
<212> TYPE: DNA
<213> ORGANISM: Artificial Sequence
<220> FEATURE:
<223> OTHER INFORMATION: primer

<400> SEQUENCE: 38
gggaaaccta gggtgtggat                                                 20
```

-continued

```
<210> SEQ ID NO 39
<211> LENGTH: 19
<212> TYPE: DNA
<213> ORGANISM: Artificial Sequence
<220> FEATURE:
<223> OTHER INFORMATION: primer

<400> SEQUENCE: 39
gacggaaaga tgtggtgtg                                            19

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
agacggaagt tcttggtgta gg                                        22
```

DENTAL PRETREATMENT MATERIAL AND DENTAL TISSUE REGENERATION KIT

CROSS REFERENCE TO RELATED APPLICATIONS

This application is a national stage application, filed under 35 U.S.C. § 371, of International Application No. PCT/JP2017/013572, filed Mar. 31, 2017, which claims priority to Japanese Application No. 2016-072306, filed Mar. 31, 2016, the contents of both of which as are hereby incorporated by reference in their entirety.

BACKGROUND

Technical Field

The present invention relates to a dental pretreatment material for promoting regeneration of dental pulp, dentin, and periapical tissue. The present invention also relates to a dental tissue regeneration kit including the dental pretreatment material.

Description of Related Art

The present inventors have disclosed that some methods for treating caries and dental pulp disease through regeneration of dental pulp and dentin by use of dental pulp stem cells are safe and effective (Patent Documents 1, 2, and 3).

The average lifetime of teeth is said to be 57 years at present. To enable a person to chew with his/her own teeth throughout the lifetime, the lifetime of teeth needs to be prolonged by 20 years or more. Despite "8020 Campaign" (to keep 20 teeth or more at the age of 80 years), people aged 80 keep about 8 teeth on average, and the number of remaining teeth of elderly people has hardly increased. It is therefore needed to enable regeneration of dental pulp and other tissues by use of dental pulp stem cells derived from an individual of advanced age.

The cytoplasm of a dental pulp stem cell of an individual of advanced age is generally the same as that of a dental pulp stem cell of an individual of young age. However, autologous transplantation of aged dental pulp stem cells into the root canal of a tooth of an aged canine does regenerate dental pulp and dentin, but with a delay, as compared to autotransplantation of young dental pulp stem cells (Non-Patent Document 1). Regarding the mechanism of regeneration of dental pulp, it has been revealed that transplanted dental pulp stem cells do not differentiate directly, but secrete trophic factors to cause migration of stem cells from the niche of periodontal tissue into a tooth, and that the migration of the stem cells promotes proliferation, anti-apoptotic effect, angiogenesis, and neuranagenesis to cause regeneration of the dental pulp (Non-Patent Document 2). The delay in regeneration of dental pulp at an advanced age is deemed to be caused by attenuation of migratory capacity, proliferative capacity, and anti-apoptotic potential of the stem cells derived from the niche of periodontal tissue, and senescence of the niche is suggested (Non-Patent Document 1).

It has been known that in general, regenerative potential and homeostatic activity deteriorates drastically with advancing age, causing dysfunction of various organs. If this phenomenon occurs in a muscle, the cause is deemed to be a change in signal of the stem-cells niche. It is further suggested that senescence of niche occurs also in tissues in the whole body.

As a result of recent animal tests, CCL11/Eotaxin has been identified as a chemokine promoting the senescence of the niche. CCL11/Eotaxin is contained in blood and circulated throughout the whole body to reduce regeneration of central nerves and to deteriorate cognitive function. On the other hand, it has been revealed that systemic administration of a CCL11-neutralizing antibody enables recovery of neurogenesis (Non-Patent Document 3). It has been also revealed that age-related cardiac hypertrophy is caused by a decrease in blood levels of GDF11, and that intravenous injection of GDF11 can improve the age-related cardiac hypertrophy (Non-Patent Document 4). Further, it has been reported that GDF11 increases revascularization and neurogenesis of a senescent brain (Non-Patent Document 5), and enhances the structure and function of a senescent skeletal muscle (Non-Patent Document 6).

Meanwhile, trypsin is used, as a pharmaceutical, to normalize a wound surface through resolution of a necrotic tissue, a clot, and/or a denatured protein, thereby facilitating the activity of an antibiotic (Non-Patent Document 7). A prior art reference teaches that trypsin is used to clean a root canal (Patent Document 4). However, no prior art reference teaches that trypsin is applicable to regeneration of dental pulp.

CCL11 transduces a signal via CCR3 as a receptor (Non-Patent Document 8). It is presumed that a CCL11-neutralizing antibody functions to inhibit CCL11 from binding to CCR3, and that a CCR3 antagonist also functions in a similar manner. However, no prior art reference teaches that a CCL11-neutralizing antibody or a CCR3 antagonist is applicable to regeneration of dental pulp.

Moreover, while GDF11 binds to type I TGF-beta superfamily receptors ACVR1B (ALK4), TGFBR1 (ALK5), and ACVR1C (ALK7), signals are transmitted by ALK4 and ALK5 (Non-Patent Document 9). Slight expression of GDF11 is observed in a layer of odontoblasts (Non-Patent Document 10). GDF11 gene transfer into exposed dental pulp induces dentin formation (Non-Patent Document 11). However, it is not clear how GDF11 and ALK5, which is a receptor of GDF11, function during dental pulp regeneration in a pulp ectomized root canal.

PATENT DOCUMENTS

Patent Document 1: Japanese Patent No. 5621105
Patent Document 2: Japanese Patent No. 5748194
Patent Document 3: Japanese Unexamined Patent Publication No. 2014-168714
Patent Document 4: Japanese Unexamined Patent Publication (Japanese Translation of PCT Application) No. 2009-513227

Non-Patent Documents

Non-Patent Document 1: Iohara K., Murakami M., Nakata K., Nakashima M, Age-dependent decline in dental pulp regeneration after pulpectomy in dogs. Exp. Gerontol. 52:39-45, 2014.
Non-Patent Document 2: Iohara K., Murakami M., Takeuchi N., Osako Y., Ito M., Ishizaka R., Utunomiya S., Nakamura H., Matsushita K., Nakashima M., A novel combinatorial therapy with pulp stem cells and granulocyte colony-stimulating factor for total pulp regeneration. Stem Cells Transl. Med. 2(7): 521-533, 2013.
Non-Patent Document 3: Villeda S. A., et al., The ageing systemic milieu negatively regulates neurogenesis and cognitive function. Nature. 477(7362):90-94, 2011.

Non-Patent Document 4: Loffredo F. S., et al., Growth differentiation factor 11 is a circulating factor that reverses age-related cardiac hypertrophy. Cell. 153(4): 828-839, 2013.

Non-Patent Document 5: Katsimpardi L., et al., Vascular and neurogenic rejuvenation of the aging mouse brain by young systemic factors. Science. 344(6184):630-634, 2014.

Non-Patent Document 6: Sinha M., et al., Restoring systemic GDF11 levels reverses age-related dysfunction in mouse skeletal muscle. Science. 344(6184):649-52, 2014.

Non-Patent Document 7: Noguchi Y., et al, The Japanese journal of dermatology and venereology, 64, 497-506, 1954.

Non-Patent Document 8: Kitaura M., et al., Molecular cloning of human eotaxin, an eosinophil-selective CC chemokine, and identification of a specific eosinophil eotaxin receptor, CC chemokine receptor 3. J Biol Chem. 271(13): 7725-30, 1996.

Non-Patent Document 9: Andersson O., et al., Growth differentiation factor 11 signals trough the transforming growth factor-β receptor ALK5 to regionalize the anterior-posterior axis. EMBO reports. 7(8): 831-7, 2006.

Non-Patent Document 10: Nakashima M., et al., Expression of growth/differentiation factor 11, a new member of the BMP/TGF beta superfamily during mouse embryogenesis. Mech Dev. 80(2):185-9, 1999.

Non-Patent Document 11: Nakashima M., et al., Induction of dental pulp stem cell differentiation into odontoblasts by electroporation-mediated gene delivery of growth/differentiation factor 11 (Gdf11). Gene Ther. 9(12):814-8, 2002.

BRIEF SUMMARY

The present invention has been made in view of the foregoing problems, and attempts to provide a dental pretreatment material suitable for dental tissue regeneration by use of dental pulp stem cells. In particular, the present invention attempts to provide a dental pretreatment material enabling effective dental tissue regeneration even in the case of autologous transplantation or allogeneic transplantation of dental pulp stem cells into an individual of middle or advanced age. The present invention also attempts to provide a dental tissue regeneration kit including the dental pretreatment material. Further, the present invention attempts to provide a root canal filler enabling effective dental tissue regeneration even in the case of transplantation of dental pulp stem cells derived from an individual of middle or advanced age.

A dental pretreatment material for dental tissue regeneration of the present invention includes a serine protease.

A dental tissue regeneration kit of the present invention includes: the dental pretreatment material of the present invention; and a root canal filler including dental pulp stem cells and an extracellular matrix, and configured to be inserted into a root canal.

A root canal filler of the present invention includes autologous or allogeneic dental pulp stem cells, an extracellular matrix, and an ALK5 inhibitor.

A root canal filler of the present invention includes autologous or allogeneic dental pulp stem cells, an extracellular matrix, and a CCR3 antagonist.

A root canal filler of the present invention includes autologous or allogeneic dental pulp stem cells, an extracellular matrix, and a CCL11-neutralizing antibody.

The present invention makes it possible to effectively regenerate dental tissue even when autologous dental pulp stem cells are transplanted into an individual of middle or advanced age.

DETAILED DESCRIPTION OF VARIOUS EMBODIMENTS

Figure 1:
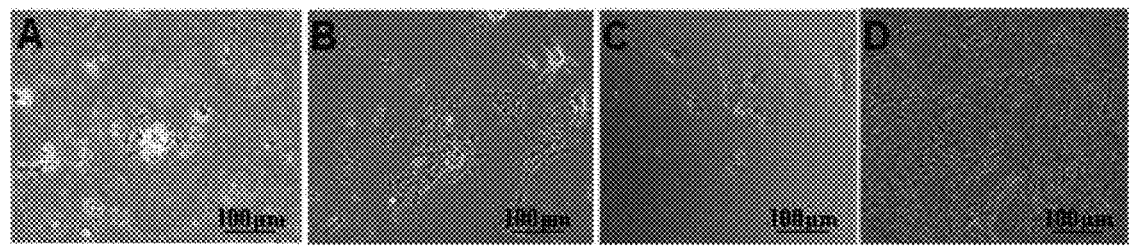
FIG. 1 includes photographs A to D, which show morphological observation of canine dental pulp stem cells by an isolation method using G-CSF-induced mobilization. Specifically, Photographs A and B show the stem cells on day 2 and day 7 following culture of the dental pulp stem cells, respectively. Photograph C shows the stem cells on day 2 following the isolation. Photograph D shows seventh-passage mobilized dental pulp stem cells on day 3.

Embodiments of the present invention will now be described specifically with reference to the attached drawings. Note that the following embodiments are described for better understanding of the principles of the present invention, and that the scope of the present invention is not limited to the following embodiments. Other embodiments corresponding to the following embodiments of which a configuration is appropriately replaced by the skilled person are also included in the scope of the present invention.

According to this embodiment, a dental pretreatment material for dental tissue regeneration includes a serine protease. According to this embodiment, a dental tissue regeneration kit for dental tissue regeneration includes one of a CCL11-neutralizing antibody and a CCR3 antagonist that suppress CCL11, or an ALK5 inhibitor inhibiting signal transmission of GDF11.

The term "dental tissue regeneration" as used herein refers to regeneration of tissue including at least one of dental pulp, dentin, or periapical tissue.

Age-related changes occur in teeth and periodontal tissue. Specifically, the cementum increases in thickness with aging. In particular, the thickness of the cementum increases significantly in a periapical region. Further, aging causes calcification of the periodontal fibers of a periodontal ligament. The dental pretreatment material is to be used before insertion of a root canal filler that includes dental pulp stem cells and an extracellular matrix into a root canal. The term "pretreatment" as used herein means injection of a liquid containing a serine protease into a root canal. Using the dental pretreatment material enables a treatment to degradate thick cementum and a calcified periodontal ligament. Using the dental pretreatment material enables a treatment to inactivate an inhibitor that inhibits tissue regeneration in a tooth or a periodontal tissue, or a treatment to activate a regeneration stimulating factor.

A serine protease is a protease (an enzyme which performs proteolysis) having, as a catalytic residue, a serine residue that performs nucleophilic attack. Serine proteases are classified, according to amino acid sequence and similarity of tertiary structure, into subtilisin-like serine proteases and chymotrypsin-like serine proteases. Examples of the former include subtilisin BPN', thermitase, proteinase K, lantibiotic peptidase, kexin, and cucumisin. Examples of the latter include trypsin, chymotrypsin, thrombin, Xa factor, and elastase. The serine protease is preferably a chymotrypsin-like serine protease, and more preferably, trypsin.

It is preferable to use the dental pretreatment material for an individual of middle or advanced age before insertion of a root canal filler including dental pulp stem cells in a root canal of the individual. However, the dental pretreatment material is also usable in the case of using dental pulp stem cells derived from an individual of young age. An individual of middle age is not particularly limited, and refers to, for example: a human from 30 to 49 years of age; a rat from 30 to 39 weeks of age; and a canine from 3 to 4 years of age. An individual of advanced age is not particularly limited, and refers to, for example: a human over 50 years old; a rat over 40 weeks old; and a canine over 5 years old. Therefore, a human individual of middle or advanced age as used herein indicates an individual over 30 years old. A rat individual of middle or advanced age as used herein indicates an individual over 30 weeks old. A canine of middle or advanced age indicates an individual over 3 years old.

The dental pretreatment material may contain the serine protease at any concentration as long as the dental pretreatment material enables a treatment to decompose thick cementum and a calcified periodontal membrane. For example, the concentration of the serine protease may range from 50 µg/ml (0.05%) to 500 µg/ml (0.5%), and preferably from 100 µg/ml (0.1%) to 300 µg/ml (0.3%).

The period of time during which the dental pretreatment material is allowed to remain in a root canal is not particularly limited as long as the dental pretreatment material enables a treatment to degradate thick cementum and a calcified periodontal ligament. For example, the period of time may be from 3 minutes to 30 minutes, preferably from 5 minutes to 20 minutes, and more preferably 10 minutes.

The dental pretreatment material according to this embodiment may include nanobubbles, in addition to the serine protease. The nanobubbles each include a vesicle comprised of lipid and a gas or a gas precursor filling the vesicle. The nanobubble may have any diameter. The diameter ranges, for example, from 10 nm to 500 nm, and preferably from 100 nm to 400 nm. The diameter of the nanobubble can be measured by, for example, a nanoparticle distribution measuring apparatus (SALD-7100, Shimadzu Corporation). The lipid composition, charged state, density, weight, particle size, and other properties of the nanobubbles can be appropriately designed. The lipid to be used for preparing the vesicle is not particularly limited, but it is comprised of a membrane constituent containing lipids. Examples of the lipids include phospholipid, glycoglycerolipid, glycosphingolipid, and cationic lipids, which include the foregoing lipids containing a primary amino group, a secondary amino group, a tertiary amino group, or a quaternary ammonium group introduced therein.

If the dental pretreatment material includes nanobubbles, the concentration of the nanobubbles is indicated by the number of the nanobubbles in the dental pretreatment material. The concentration of the nanobubbles is not particularly limited, and may be 1,000 nanobubbles/cm$^3$ to 10,000 nanobubbles/cm$^3$, for example. The concentration of the nanobubbles can be quantitatively analyzed by electron spin resonance (ESR), for example.

The dental tissue regeneration kit includes the dental pretreatment material described above, a root canal filler that includes dental pulp stem cells and an extracellular matrix, and is configured to be inserted into a root canal.

The root canal filler includes, for example, autologous or allogeneic dental pulp stem cells, an extracellular matrix, and an ALK5 inhibitor.

The root canal filler includes, for example, autologous or allogeneic dental pulp stem cells, an extracellular matrix, and a CCR3 antagonist.

The root canal filler includes, for example, autologous or allogeneic dental pulp stem cells, an extracellular matrix, and a CCL11-neutralizing antibody.

Alternatively, the root canal filler includes autologous or allogeneic dental pulp stem cells, an extracellular matrix, and a mixture of at least two of an ALK5 inhibitor, a CCR3 antagonist, and a CCL11-neutralizing antibody. As will be described later in examples, the ALK5 inhibitor and the CCR3 antagonist are characterized in that: although both are effective in dental pulp regeneration, the ALK5 inhibitor is more effective in angiogenesis than the CCR3 antagonist, while the CCR3 antagonist is more effective in neuropoiesis than the ALK5 inhibitor. For this reason, the root canal filler may include, for example, autologous or allogeneic dental pulp stem cells, an extracellular matrix, and a mixture of the ALK5 inhibitor and the CCR3 antagonist. In the case of using a mixture of the ALK5 inhibitor and the CCR3 antagonist, the mixing ratio between the ALK5 inhibitor and the CCR3 antagonist is not particularly limited, and may range, for example, from 10% by weight (wt. %):90 wt. % to 90 wt. %:10 wt. %.

The ALK5 inhibitor is not limited to any particular compound. Examples of the ALK5 inhibitor include the following compounds:

[Chem. 1]

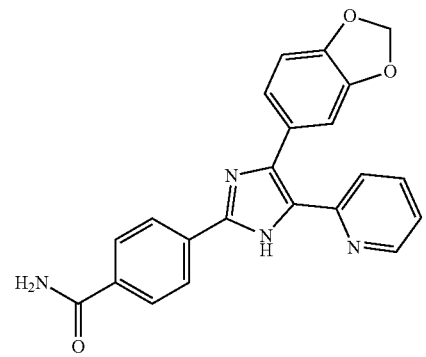

[Chem. 2]

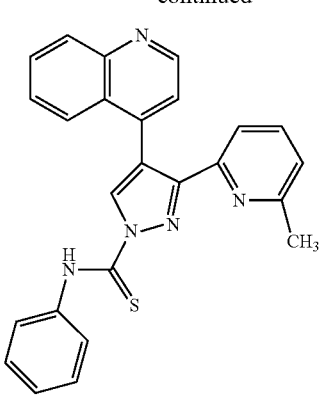

[Chem. 3]

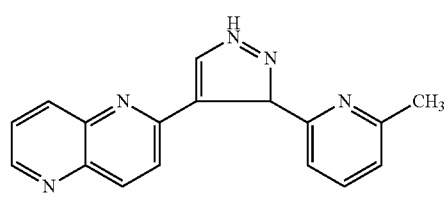

The CCR3 antagonist is not limited to any particular compound. Examples of the CCR3 antagonist include the following compounds:

[Chem. 4]

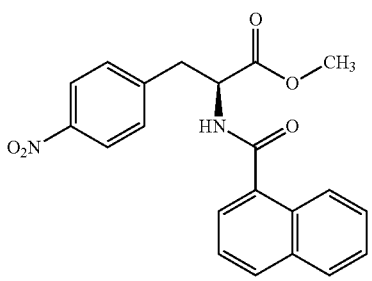

[Chem. 5]

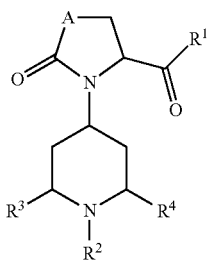

Here, A is $CH_2$ or O, $R^1$ is NHR (wherein R is C, 1-C6 alkyl), $R^2$ is C, 1-C6 alkylene-phenyl, $R^3$ is H or C1-C6 alkyl, and R4 is H or C1-C6 alkyl.

CCL11 transmits a signal while using CCR3 as a receptor. An anti-CCL11 neutralizing antibody acts to inhibit the CCL11 from binding to CCR3. A CCR3 antagonist acts in a similar manner. A commercially available anti-CCL11 neutralizing antibody may be used in the present invention.

According to this embodiment, one of the CCL11-neutralizing antibody and the CCR3 antagonist that suppress CCL11, or the ALK5 inhibitor that inhibits the signal transmission of GDF11 is contained at a concentration ranging, for example, from 50 ng/ml to 50 µg/ml, and preferably from 10 µg/ml to 30 µg/ml.

The dental pulp stem cells are not particularly limited, and include, for example, at least one kind selected from CD105-positive cells, CXCR4-positive cells, SSEA-4-positive cells, FLK-1-positive cells, CD31-negative and CD146-negative cells, CD24-positive cells, CD150-positive cells, CD29-positive cells, CD34-positive cells, CD44-positive cells, CD73-positive cells, CD90-positive cells, FLK-1-positive cells, G-CSFR-positive cells, and SP cells. For example, the SP cells are CXCR4-positive cells, SSEA-4-positive cells, FLK-1-positive cells, CD31-negative and CD146-negative cells, CD24-positive cells, CD105-positive cells, CD150-positive cells, CD29-positive cells, CD34-positive cells, CD44-positive cells, CD73-positive cells, CD90-positive cells, FLK-1-positive cells, or G-CSFR-positive cells.

The extracellular matrix is not particularly limited, and includes at least one of collagen, artificial proteoglycan, gelatin, hydrogel, fibrin, phosphophoryn, heparan sulfate, heparin, laminin, fibronectin, alginic acid, hyaluronic acid, chitin, PLA, PLGA, PEG, PGA, PDLLA, PCL, hydroxyapatite, β-TCP, calcium carbonate, titanium, gold or extracellular matrix derived from pulp stem/progenitor cells.

In addition to the dental pulp stem cells and the extracellular matrix, the root canal filler can contain a cell migration factor. The cell migration factor includes, for example, at least one of G-CSF, SDF-1, bFGF, TGF-β, NGF, PDGF, BDNF, GDNF, EGF, VEGF, SCF, MMP3, Slit, GM-CSF, LIF or HGF.

The dental pulp stem cells may be isolated by any method. For example, SP cells are labeled with Hoechst 33342, and fractions that strongly release this dye are separated using Hoechst Blue and Hoechst Red through a flow cytometer. Alternatively, the isolation may be performed by, for example, use of an antibody against a membrane surface antigen specific to stem cells. Specifically, magnetic beads are used in this separation. Alternatively, the isolation may be performed by use of, for example, a membrane-isolation-type culture device. The membrane-isolation-type culture device includes an upper structure comprised of a vessel whose bottom surface is at least partially made of an isolation membrane having pores that allow stem cells to permeate therethrough, and a lower structure comprised of a vessel retaining a medium in which the membrane of the upper structure is immersed. The disclosure of Domestic Re-Publication No. 2012/133803 which is the publication of a patent application of the present inventors is incorporated by reference herein. The isolation membrane includes a base material film made of a hydrophobic polymer and a functional layer formed through covalent bond of a hydrophilic polymer with a surface of the base material film. The size of the pores is, for example, 3 µm to 10 and the density is, for example, $1 \times 10^5$ to $4 \times 10^6$ pores/cm$^2$. The medium is not particularly limited, and Dulbecco's modified Eagle's medium, EBM 2 or the like may be used as the medium, for example.

Example 1

(Characteristics of Dental Pulp Stem Cells of Canine of Middle or Advanced Age)

Under general anesthesia, a maxillary cuspid tooth was extracted from a female canine (weighing 10 kg) at 5 years of age. An incision is made in the extracted tooth by a diamond bur so that the incision extended vertically from the crown part to the root part while not reaching the dental pulp. Within one hour, the tooth was transported in a special transport container under temperature control, with use of Hanks solution, as a transporting liquid, containing 20 µg/ml of gentamicin (GENTALOL (registered trademark), Nitten Pharmaceutical Co., Ltd.) and 0.25 µg/ml of amphotericin B (FUNGIZONE (registered trademark), Bristol-Myers Squibb.). In a clean bench, the dental pulp was extracted and cut into small pieces, to which 5 ml of a 0.04 mg/ml liberase solution was added. Following mixing by inversion, the resultant mixture was shaken on Thermomixer Comfort (Eppendorf AG.) at 37° C. and 500 rpm for 30 minutes. After the shaking, the mixture was suspended 30 times, and then, centrifuged with a cooling centrifuge with built-in isolator (TOMY SEIKO CO., LTD.) at 200 rpm for 1 minute. A supernatant in the centrifuge tube was collected. The supernatant was centrifuged at 2,000 rpm for 5 minutes. DMEM containing 10% autologous canine serum was added to the precipitated cells, and the resultant mixture was suspended, followed by centrifugation at 2,000 rpm for 5 minutes. The cells were precipitated again, and 5 ml of DMEM containing 10% autologous canine serum was added to the precipitated cells. The resultant mixture was suspended 30 times. The cell suspension was mixed with the same amount of Trypan blue (0.4%, SIGMA), and suspended 10 times. Viable cells were counted. The remaining suspension was evenly seeded in T25 flasks and cultured in a $CO_2$ incubator (Panasonic Corporation) (37° C., 5% $CO_2$) to observe the morphology. After reaching 60-70% confluence, the cells were subcultured until the seventh passage, and frozen.

To determine a cell surface antigen, the fifth passage cells were dispersed in PBS containing 20% serum to achieve a density of $1 \times 10^7$ cells/ml. The mixture was allowed to react with Blocking (FcγIII/II receptor blocking) at 4° C. for 20 minutes. Thereafter, the following stem cell surface markers were allowed to react at 4° C. for 90 minutes in a dark place: CD31 (PE) (JC70A) (Dako), CD29 (PE-Cy7) (HMb1-1) (eBioscience), CD44 (Phycoerythrin-Cy7, PE-Cy7) (IM7) (eBioscience), CD73 (APC) (AD2) (BioLegend), CD90 (PE) (YKIX337.217) (eBioscience), CD105 (PE) (43A3) (BioLegend), CD146 (FITC) (sc-18837) (Santa Cruz), CXCR4 (FITC) (12G5) (R&D), and G-CSF-R (Alexa 488) (S1390) (Abcam). As negative controls, the following was used: mouse IgG1 negative control (AbD Serotec), mouse IgG1 negative control (fluorescein isothiocyanate, FITC) (MCA928F) (AbD Serotec), mouse IgG1 negative control (Phycoerythrin-Cy7, PE-Cy7) (299Arm) (eBioscience), and mouse IgG1 negative control (Alexa 647) (MRC OX-34) (AbD Serotec). Positive expression rates were compared using a flow cytometer (FACS Aria II (BD bioscience)).

The second passage dental pulp cells isolated from a dental pulp tissue of the canine of middle or advanced age (Photographs A and B in FIG. 1) were plated on the upper structure of a membrane migration separation device. About 3% of the plated cells migrated due to G-CSF concentration gradient, and adhered to the well. After two days, satellate-shaped cells having short process were observed (Photograph C in FIG. 1). The cells gradually formed colonies and reached 70% confluence after approximately ten days. The cells were subcultured until the seventh passage (Photograph D in FIG. 1), so that at least $8 \times 10^6$ cells were obtained. The cells were dispensed to be divided into groups each including $1 \times 10^6$ cells to be cryopreserved. The cryopreserved cells of the seventh passage were thawed. The survival fraction was 80% or higher. Further, the cells were cultured after being thawed. On day 3 following the thawing, the cells maintained generally the same shape as that prior to the cryopreservation.

The cryopreserved seventh passage cells were thawed to observe expression of surface antigen by flow cytometry. The positive expression rates for CD29, CD44, CD73, CD90, and CD105 were 95% or higher, whereas the cells were negative for CD31. It was therefore presumed that many stem/progenitor cells were contained. Further, the positive expression rates for CXCR4 and G-CSFR were 7.4% and 60.0%, respectively (Table 1).

TABLE 1

|  | Dental pulp stem cells membrane-seperated from individual of advanced age (%) |
| --- | --- |
| CD29 | 93.1 |
| CD31 | 0.8 |
| CD44 | 93.5 |
| CD73 | 90.3 |
| CD90 | 98.8 |
| CD105 | 95.0 |
| CD146 | 4.8 |
| CXCR4 | 7.4 |
| G-CSFR | 60.0 |

(Microenvironment of Tooth and Periodontal ligament of Middle or Advanced Aged Dogs)

Under general anesthesia, a dog of middle or advanced age and a dog of young age were slaughtered. A maxillary second incisor was harvested from each canine such that the incisor contained periapical region. Following the harvest, 5 µm paraffin sections of longitudinal cross section were prepared according to a common method. The paraffin sections were H-E stained to undergo morphological observation. The paraffin sections were stained with Masson Trichrome, or immunohistologically stained with Vimentin or versican (Vcan). Specifically, after deparaffinization, the sections were allowed to react with a 3% hydrogen peroxide solution/ethanol for 10 minutes so that endogenous peroxidase was inhibited. The sections were blocked by being treated with 10% goat serum for 60 minutes. Thereafter, as primary antibodies, mouse anti-human vimentin (Abcam, 1:100) and mouse anti-human versican (Millipore, 1:100) were allowed to react overnight at 4° C. Next day, antigens were detected with DAB by use of DAKO LSABII Kit. Nuclear stain was carried out using hematoxylin. The deparaffinized 5 µm sample sections were stained with Masson Trichrome to evaluate calcification.

Figure 2:
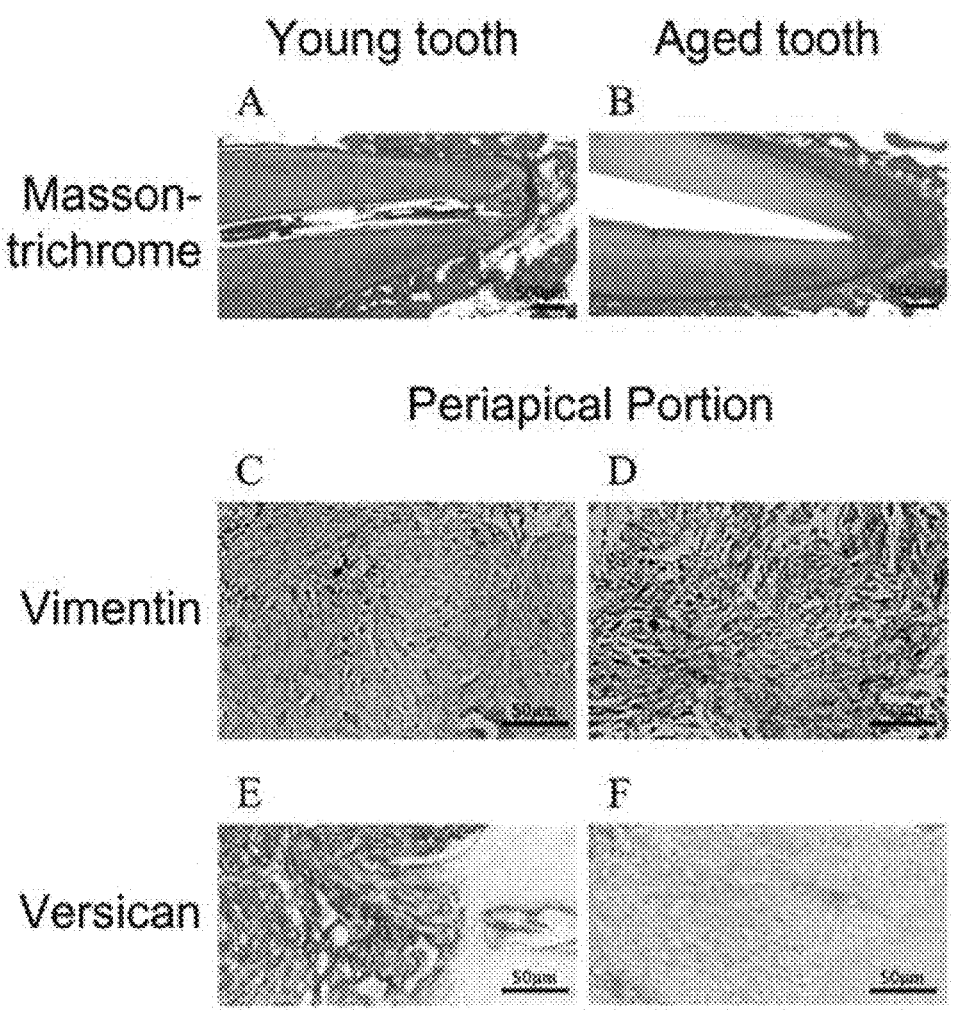
FIG. 2 shows comparison between a normal tooth of a canine of middle or advanced age and a normal tooth of a canine of young age. Specifically, Photographs A, C and E show the tooth of young age and Photographs B, D, and F show the tooth of middle or advanced age. Photographs A and B are Masson Trichrome stain images, Photographs C and D are Vimentin immunostaining images, and Photographs E and F are Versican immunostaining images.

As a result of the Masson Trichrome stain, it was confirmed that the cementum of the incisor of the canine of middle or advanced age had thickened and ossified remarkably, and the periodontal ligament was constricted (Photographs A and B in FIG. 2). Strong expression of vimentin was observed in the periapical region of the tooth of middle or advanced aged dog, whereas slight expression of vimentin was observed in that of young aged dog (Photographs C and D in FIG. 2). On the other hand, expression of versican was stronger in the periapical region of the tooth of young aged dog than in that of middle or advanced aged dog (Photographs E and F in FIG. 2).

(Dental Pulp Regeneration following Pulpectomy by Transplantation of Dental Pulp Stem Cells from Middle or Advanced Aged Dog)

Under general anesthesia, anterior teeth of upper and lower jaws of middle or advanced aged dog and young aged dog were pulpectomized. For each tooth, the root canal was enlarged with #50-55 to the apex, and was irrigated alternately with a 5% sodium hypochlorite solution and a 3% hydrogen peroxide solution, followed by washing with physiologic saline. The root canal was completely dried with paper points, and hemorrhage was controlled. The root canal was completely closed with a temporary seal of cement and resin. After 7 to 14 days following the pulpectomy, the temporary seal was removed, and the root canal underwent the alternate washing, and then, washing with physiologic saline. Smear clean (3% EDTA) was then allowed to react for 2 minutes. The root canal was then further washed with physiologic saline, and dried. Thereafter, FRANCETIN•T•POWDER (2500 USP of crystalized trypsin per 10 mg) (MOCHIDA PHARMACEUTICAL CO., LTD.) at a concentration of 50 µg/ml (0.05%) or 500 µg/ml (0.5%) was allowed to react in the root canal for 10 minutes or 30 minutes. Washing with physiologic saline was then performed. As a control, a tooth on the opposite side was not treated. Further, FRANCETIN•T•POWDER was mixed with a nanobubble liquid into a 50 µg/ml (0.05%) solution. The solution was allowed to act in a similar manner for 10 minutes, followed by washing with physiologic saline. A root canal filler was prepared by suspending $1 \times 10^6$ autologous dental pulp stem cells, which had been membrane-isolated, in 40 µl of a scaffold (Koken Atelocollagen Implant, KOKEN CO., LTD.), and by suspending 3 µl of 100 µg/ml G-CSF (NEUTROGIN, Chugai Pharmaceutical Co., Ltd.). The root canal filler prepared was injected into each root canal such that no air bubbles were contained. The mobilized dental pulp stem cells were isolated using the membrane-isolation-type culture device described above. A hemostatic gelatin sponge (Spongel) was put on the root canal filler. The cavity was completely sealed with cement and resin. On day 14 following the transplantation, the teeth were extracted. According to a common method, 5 µm paraffin sections of longitudinal cross section were prepared. The paraffin sections were then H-E stained to undergo morphological observation. To analyze angiogenesis, the sections were immunostained with BS-1 lectin. Amounts of regenerated dental pulp of four sections were measured for each sample, and an average amount of four samples was determined as the amount of regenerated dental pulp of the sample.

Figure 3:
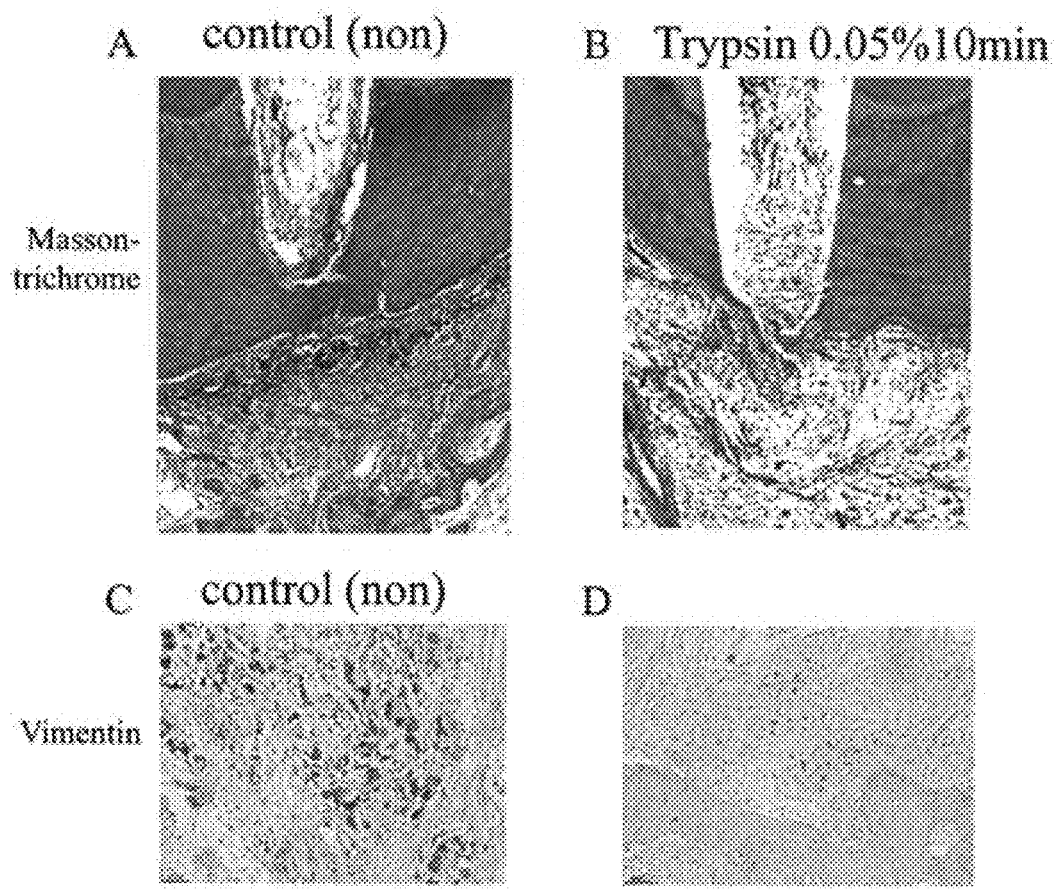
FIG. 3 shows images of periapical tissue after 14 days following autologous transplantation of a root canal filler into a pulpectomized root canal, the root canal filler including dental pulp stem cells of a canine of middle or advanced age and atelocollagen. Specifically, Photographs A and C show periodontal tissue provided with no pretreatment, whereas Photographs B and D show periodontal tissue treated with a pretreatment material including 0.05% trypsin for 10 minutes. Photographs A and B are Masson Trichrome staining images. Photographs C and D are Vimentin immunostaining images.
Figure 4:
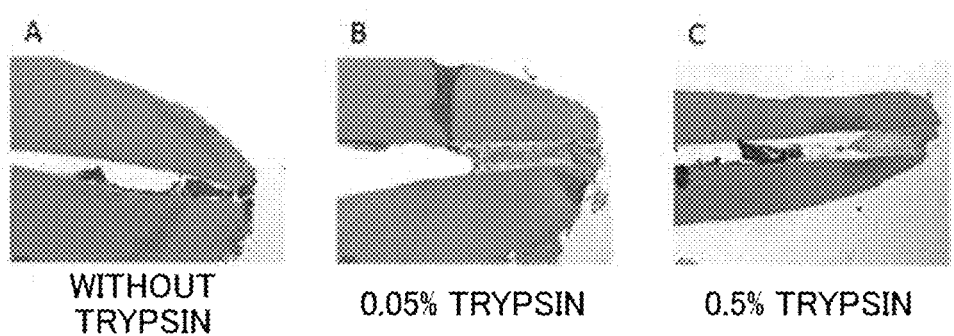
FIG. 4 includes photographs that (on day 14 following transplantation, H-E stain) show dental pulp regeneration by autologous transplantation with a root canal filler into a pulpectomized root canal, the root canal filler including dental pulp stem cells of a canine of middle or advanced age and atelocollagen. Specifically, Photographs A shows the inside of a root canal provided with no pretreatment. Photograph B shows dental pulp regeneration in a case where a pretreatment material including 50 µg/ml (0.05%) trypsin was used for 10 minutes. Photograph C shows dental pulp regeneration in a case where a pretreatment material including 500 µg/ml (0.5%) trypsin was used for 10 minutes. Graph D shows a statistical analysis of the amounts of regenerated dental pulp.
Figure 4:
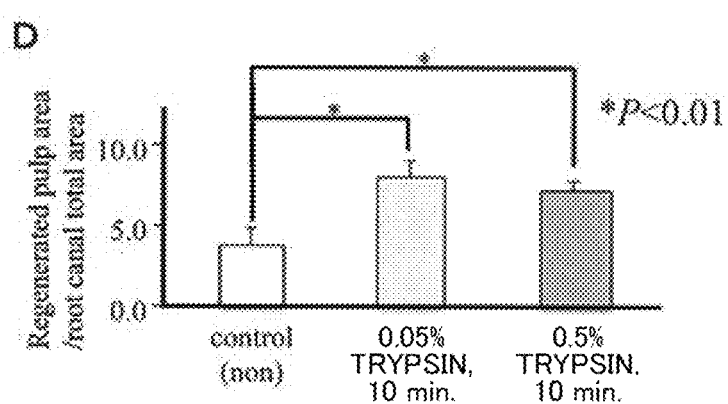
Figure 5:
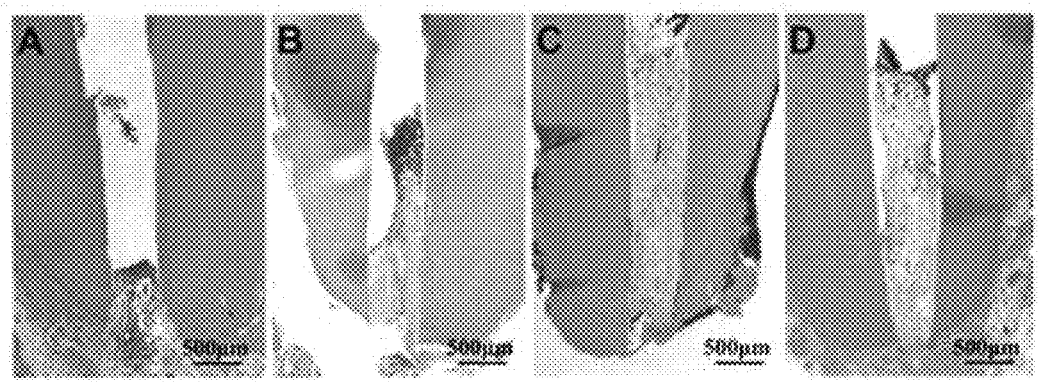
FIG. 5 includes photographs (on day 14 following transplantation, H-E stain) show dental pulp regeneration by autologous transplantation with a root canal filler into a pulpectomized root canal, the root canal filler including dental pulp stem cells of a canine of middle or advanced age and atelocollagen. Specifically, Photograph A shows dental pulp regeneration on day 14, provided with no pretreatment. Photograph B shows dental pulp regeneration on day 14 in a case where a pretreatment material including trypsin was used for 10 minutes. Photograph C shows dental pulp regeneration on day 14 in a case where a pretreatment material including trypsin was used for 30 minutes. Photograph D shows dental pulp regeneration on day 14 in a case where a pretreatment material including trypsin and nanobubbles was used for 10 minutes. Graph E shows a statistical analysis of the amounts of regenerated dental pulp.
Figure 5:
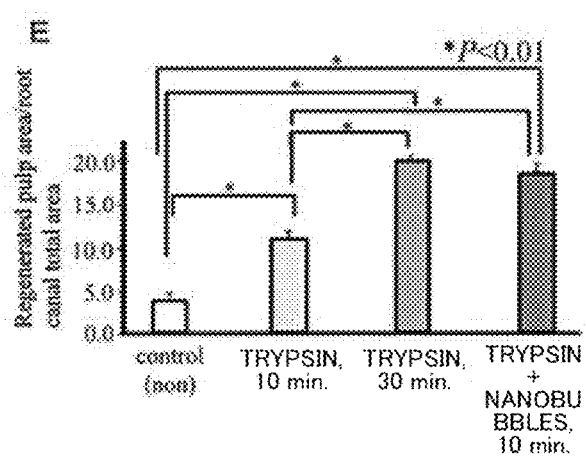
Figure 6:
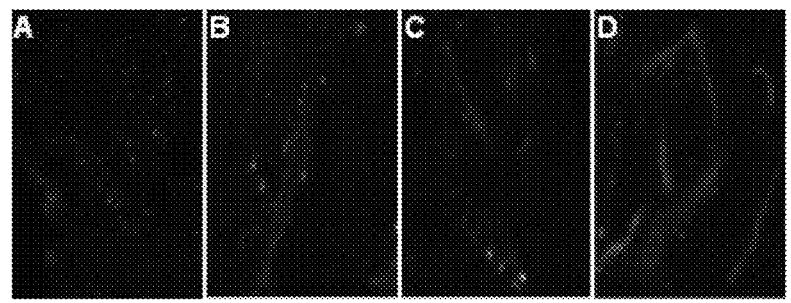
FIG. 6 includes photographs that (BS-1 lectin stain) show angiogenesis in regenerated dental pulp. Specifically, Photograph A shows dental pulp regeneration on day 14, provided with no pretreatment. Photograph B shows dental pulp regeneration on day 14 in a case where a pretreatment material including trypsin was used for 10 minutes. Photograph C shows dental pulp regeneration on day 14 in a case where a pretreatment material including trypsin was used for 30 minutes. Photograph D shows dental pulp regeneration on day 14 in a case where a pretreatment material including trypsin and nanobubbles was used for 10 minutes.

The root canal filler including atelocollagen as a scaffold, G-CSF as a migration factor, and dental pulp stem cells was injected in a pulpectomized root canal at 5 years of age in dogs. On day 14, it was observed that a small amount of dental pulp tissue was regenerated while inflammatory cell infiltration and internal resorption were absent. It has been confirmed, by means of Masson Trichrome stain and the vimentin immunostaining, that the applied trypsin decomposed the calcification in the periapical tissue (Photographs A to D in FIG. 3). Applying 50 µg/ml (0.05%) trypsin for 10 minutes prior to the injection of the root canal filler increased the amount of regenerated dental pulp by 2.5 times (Photographs A, B, and Graph D in FIG. 4). Allowing trypsin at a higher concentration of 500 µg/ml (0.5%) to react in the root canal for 10 minutes did not cause any significant difference from the case of 50 µg/ml (0.05%) trypsin (Photograph C and Graph D in FIG. 4). Applying 50 µg/ml (0.05%) trypsin for 30 minutes doubled the amount of regenerated dental pulp, as compared to the case where trypsin at the same concentration was applied for 10 minutes (Photographs B, C, and Graph E in FIG. 5). Applying 50 µg/ml (0.05%) trypsin containing nanobubbles at a rate of 50% for 10 minutes increased the amount of regenerated dental pulp by 4 times (Photograph D and Graph E in FIG. 5). Abnormality such as inflammation was not observed at the periapical region. In the regenerated dental pulp of each sample, angiogenesis was observed (Photographs B to D in FIG. 6). In particular, the dental pulp formed after trypsin treatment did not show any increase of inflammatory cells, formation of necrotic layer, or the like. These results suggest that the action of trypsin causes a significant increase in the amount of regenerated dental pulp. This can be because trypsin degradates cementum that has thickened with aging and periodontal ligament that has been calcified with aging, which facilitates migration of the stem cells resided in the periapical tissue. Moreover, it is also possible that migration of the stem cells of the organism is facilitated by growth factors and migration factors that were released by trypsin since a large amount of growth factors and a large amount of migration factors are secreted in the dentin and the cementum (Miki Y, 1987). According to the fact that abnormality caused by the trypsin treatment was not observed around the root apex, it is presumed that trypsin treatment caused only slight damage to the tissue.

Figure 7:
FIG. 7 is a photograph showing the inside of a pulpectomized root canal of a canine, the root canal having been treated with trypsin, but not having received transplantation of dental pulp stem cells.

When the inside of the pulpectomized root canal at 5 years of age in dogs was treated with 50 µg/ml (0.05%) trypsin and no dental pulp stem cells were transplanted in the root canal, no inflammation occurred around the periapical region while almost no dental pulp was regenerated (FIG. 7).

Example 2

(Induction of Dental Pulp and Dentin by Dental Pulp Stem Cells Attached to Trypsin-Treated Fine-Grained Dentin Particles)

A tooth was extracted from a dog. The cementum and dental pulp of the tooth were removed mechanically. The tooth was then rinsed with tapping water for 3 hours, and then crushed into grains. Fine grains of dentin particles having a diameter of 500 µm to 1,000 µm (fine-grained dentin) were separated by use of a sieve. The fine-grained dentin particles was treated with a mixture liquid containing chloroform and methanol at room temperature for 6 hours, and then, with LiCl (8.0 M) at 4° C. for 24 hours. The fine-grained dentin was then inactivated in distilled water at 55° C. for 24 hours. Thereafter, the fine-grained dentin were divided into six groups: group (i) treated with 0.05% trypsin for 10 minutes; group (ii) treated with 0.05% trypsin and 1 mM EDTA for 10 minutes; a group (iii) treated with 1 mM of EDTA for 10 minutes; group (iv) treated with 0.05% chymotrypsin for 10 minutes; group (v) treated with 0.1 mg/mL MMP3 for 10 minutes; and group (vi) subjected to no treatment. Three fine grains of each of the groups were mixed with $2 \times 10^5$ canine dental pulp stem cells. Each mixture underwent centrifugation at 2,000 rpm for 5 minutes, followed by culture in Dulbecco's Modified Eagle's Medium containing 10% FBS at 37° C. for 7 days in the presence of 5% $CO_2$. The culture was then fixed overnight with 4% paraformaldehyde. Paraffin sections were prepared according to a common method, and sliced into 5 µm thick ultrathin sections. The ultrathin sections underwent HE stain.

Figure 8:
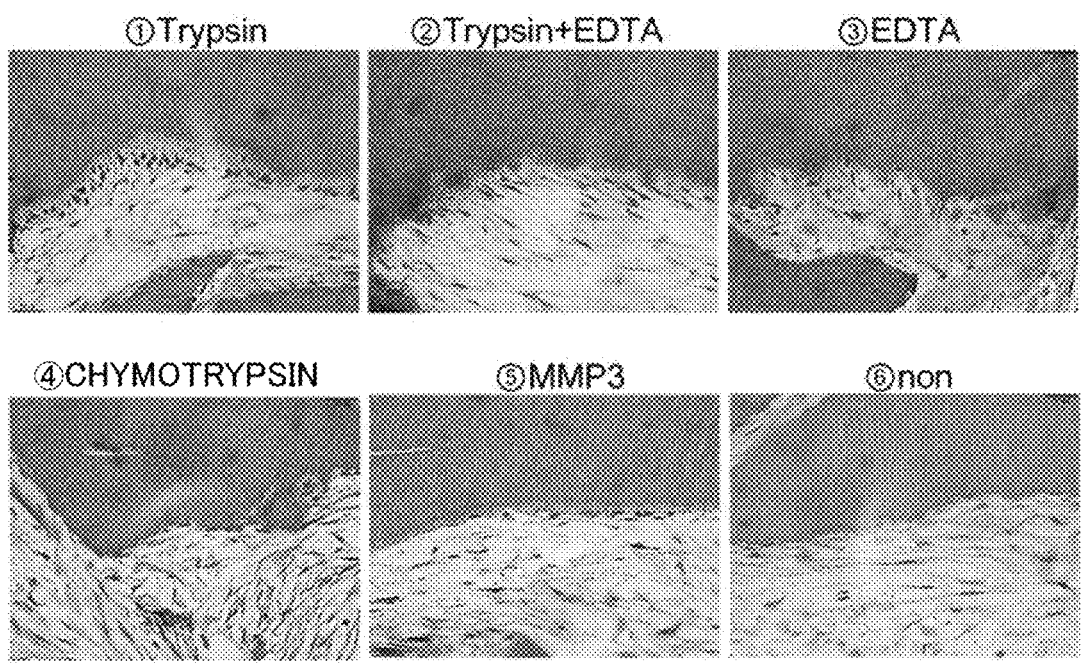
FIG. 8 includes photographs that show induction of dental pulp stem cells to dental pulp and dentin tissues in cases where fine-grained dentin treated with trypsin was used. Specifically, (i) shows cell induction with use of fine-grained dentin particle treated with 0.05% trypsin for 10 minutes; (ii) shows cell induction with use of fine-grained dentin particle treated with 0.05% trypsin and 1 mM EDTA for 10 minutes; (iii) shows cell induction with use of fine-grained dentin particle treated with 1 mM EDTA for 10 minutes; (iv) shows cell induction with use of fine-grained dentin particle treated with 0.05% chymotrypsin for 10 minutes; (v) shows cell induction with use of fine-grained dentin treated with 0.1 mg/mL MMP3 for 10 minutes; and (vi) shows cell induction with use of fine-grained dentin provided with no treatment.

The result shows the following. In the dentin of the group (i) treated with trypsin and the dentin of the group (ii) treated with trypsin and EDTA, cell adhesion was facilitated and induction of the dental pulp stem cells into the dental pulp and dentin was more promoted, as compared to the untreated denting of the group (vi) (FIG. 8). In the group (iii) treated with EDTA only, although a less number of cells adhered, induction into the dentin was promoted. The dentin of the group (iv) treated with chymotrypsin or the dentin of the group (v) treated with MMP3 were inferior in cell adhesiveness to the dentin of the group (i) treated with trypsin and the dentin of the group (ii) treated with trypsin and EDTA, while showing adhesion of a small number of cells. In the untreated group (vi), almost no cells adhered to the dentin surface (FIG. 8). These results suggest a possibility that trypsin and the combination of trypsin and EDTA promote dental pulp regeneration by releasing and activating various growth factors, differentiation factors, and any other factors that have been secreted from dental pulp stem/progenitor cells or odontoblasts in a nascent state and that are accumulated in a dentin matrix.

The mechanism of the regeneration of dental pulp and dentin by use of the root canal filler developed by the present inventor is as follows: the dental pulp stem cells contained in the root canal filler inserted in a root canal secrete trophic factors so as to cause migration of stem cells from the niche of periodontal tissue into the root canal, so that proliferation, anti-apoptotic effect, angiogenesis, and neural extension are promoted, thereby causing regeneration of dental pulp and dentin. For example, if a root canal of an individual of advanced age is to be treated, an increased thickness of the cementum and calcification of the periodontal fibers in the periapical region may inhibit the stem cells from migrating into the root canal from the periodontal tissue. Using the dental pretreatment material of the present invention enables a treatment to degradate such thickened cementum and a calcified periodontal membrane, making it less likely for the stem cells to be inhibited from migrating from the periodontal tissue into the root canal. Further, using the dental pretreatment material of the present invention allows release of various growth factors, differentiation factors, and any other factors that have been accumulated in a dentin matrix, and thus, makes it likely to promote the regeneration of dental pulp and dentin.

Example 3

(Dental Pulp Regeneration after Pulpectomy in a Case of Allogeneic Transplantation of Dental Pulp Stem Cells into Teeth of Young Aged and Middle or Advanced Aged Dogs)

Under general anesthesia, anterior teeth of upper and lower jaws of a tooth of middle or advanced aged dog (5 years old) and a tooth of young aged dog underwent a pulpectomy treatment. For each tooth, the root canal was enlarged with #50-55 to the apex, and was washed alternately with a 5% sodium hypochlorite solution and a 3% hydrogen peroxide solution, followed by washing with physiologic saline. The root canal was completely dried with paper points, and hemorrhage was controlled. The root canal was completely closed with a temporary seal of cement and resin. After 7 to 14 days following the pulpectomy, the temporary seal was removed, and the root canal underwent alternate washing and with physiologic saline. Smearclean was then allowed to react for 2 minutes. The root canal was then further washed with physiologic saline, and dried. A root canal filler was prepared by suspending 1×10$^6$ allogenic dental pulp stem cells, which had been membrane-separated, in 40 µl of a scaffold (Koken Atelocollagen Implant, KOKEN CO., LTD.), and by suspending 3 µl of a 100 µg/ml G-CSF (NEUTROGIN, Chugai Pharmaceutical Co., Ltd.). Further, an ALK5 inhibitor (SB431542, 200 ng) was added to part of the root canal filler. A CCR3 antagonist (SB328437, 200 ng) was added to another part of the root canal filler. The root canal filler with the ALK5 inhibitor or the CCR3 antagonist was injected into associated root canal such that no air bubbles were involved. A hemostatic gelatin sponge (Spongel) was put on the root canal filler. The cavity was completely sealed with cement and resin. After 14 days and 60 days following the transplantation, the teeth were extracted. According to a common method, 5 µm paraffin sections of longitudinal cross section were prepared. The paraffin sections were then H-E stained to undergo morphological observation. Amounts of regenerated dental pulp of four sections were measured for each sample, and an average amount of three samples (14-day samples) or an average amount of four samples (60-day samples) was determined to be the amount of regenerated dental pulp of the respective sample. To analyze angiogenesis, the 60-day samples were immunostained with BS-1 lectin. To analyze neurite outgrowth, the 60-day samples were immunostained with PGP 9.5.

Figure 9:
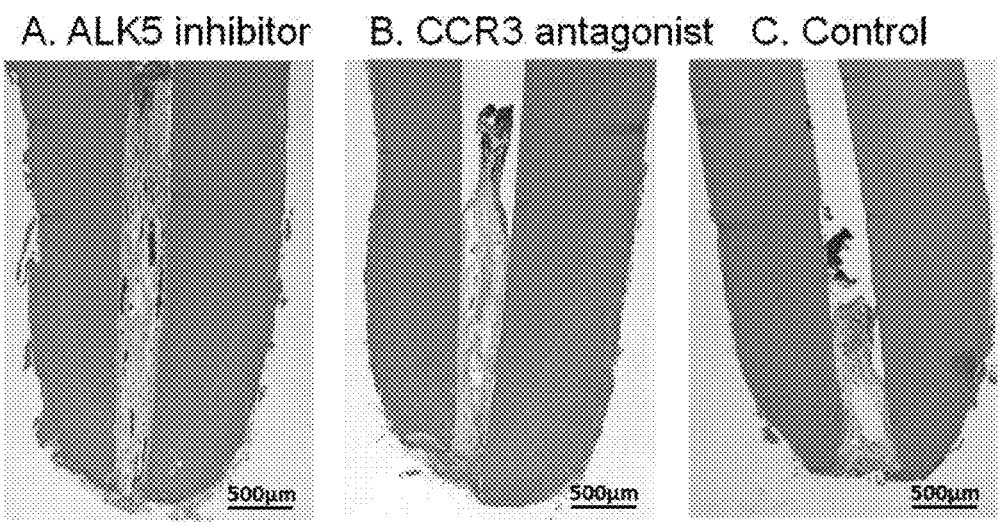
FIG. 9 includes photographs that show morphological observation after 14 days following transplantation of allogeneic dental pulp stem cells into a dog tooth of middle or advanced age. Specifically, Photograph A shows a tooth into which an ALK5 inhibitor (SB431542, 200 ng) was transplanted together with dental pulp stem cells, G-CSF, and collagen. Photograph B shows a tooth into which a CCR3 antagonist (SB328437, 200 ng) was transplanted together with dental pulp stem cells, G-CSF, and collagen. Photograph C shows a control into which only dental pulp stem cells, G-CSF, and collagen were transplanted according to a common method.
Figure 10:
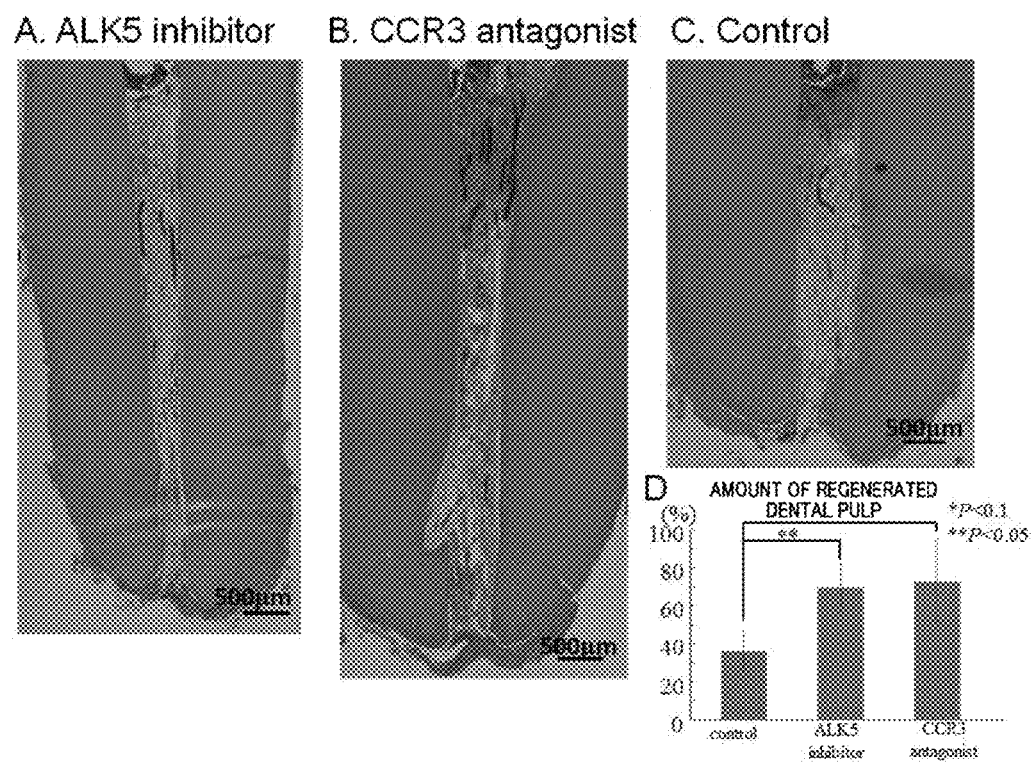
FIG. 10 includes photographs that show morphological observation, after 60 days following transplantation of autologous dental pulp stem cells into a dog tooth of middle or advanced age. Specifically, Photograph A shows a tooth into which an ALK5 inhibitor (SB431542, 200 ng) was transplanted together with dental pulp stem cells, G-CSF, and collagen. Photograph B shows a tooth into which a CCR3 antagonist (SB328437, 200 ng) was transplanted together with dental pulp stem cells, G-CSF, and collagen. Photograph C shows a control into which only dental pulp stem cells, G-CSF, and collagen were transplanted according to a common method. Graph D shows a statistical comparison of the amounts of regenerated dental pulp. *$P<0.1$, **$P<0.05$ FIG. 11 includes photographs that show angiogenesis, 60 days after transplantation of allogeneic dental pulp stem cells into a dog tooth of middle or advanced age. Specifically, Photograph A shows a tooth into which an ALK5 inhibitor (SB431542, 200 ng) was transplanted together with dental pulp stem cells, G-CSF, and collagen. Photograph B shows a tooth into which a CCR3 antagonist (SB328437, 200 ng) was transplanted together with dental pulp stem cells, G-CSF, and collagen. Photograph C shows a control into which only dental pulp stem cells, G-CSF, and collagen were transplanted according to a common method. Graph D shows a statistical comparison of the angiogenic amounts. *$P<0.1$ FIG. 12 includes photographs that show neurite outgrowth re-innervation, 60 days after transplantation of allogeneic dental pulp stem cells into a dog tooth of middle or advanced age. Specifically, Photograph A shows a tooth into which an ALK5 inhibitor (SB431542, 200 ng) was transplanted together with dental pulp stem cells, G-CSF, and collagen. Photograph B shows a tooth into which a CCR3 antagonist (SB328437, 200 ng) was transplanted together with dental pulp stem cells, G-CSF, and collagen. Photograph C shows a control into which only dental pulp stem cells, G-CSF, and collagen were transplanted according to a common method. Graph D shows a statistical comparison of the neuranagenesis amounts. **$P<0.01$ FIG. 13 includes photographs that show morphological observation, 14 days after transplantation of allogeneic dental pulp stem cells into a dog tooth of young age. Specifically, Photograph A shows a tooth into which a CCR3 antagonist (SB328437, 200 ng) was transplanted together with dental pulp stem cells, G-CSF, and collagen. Photograph B shows a control into which only dental pulp stem cells, G-CSF, and collagen were transplanted according to a common method. Graph C shows a statistical comparison of the amounts of regenerated dental pulp.
Figure 11:
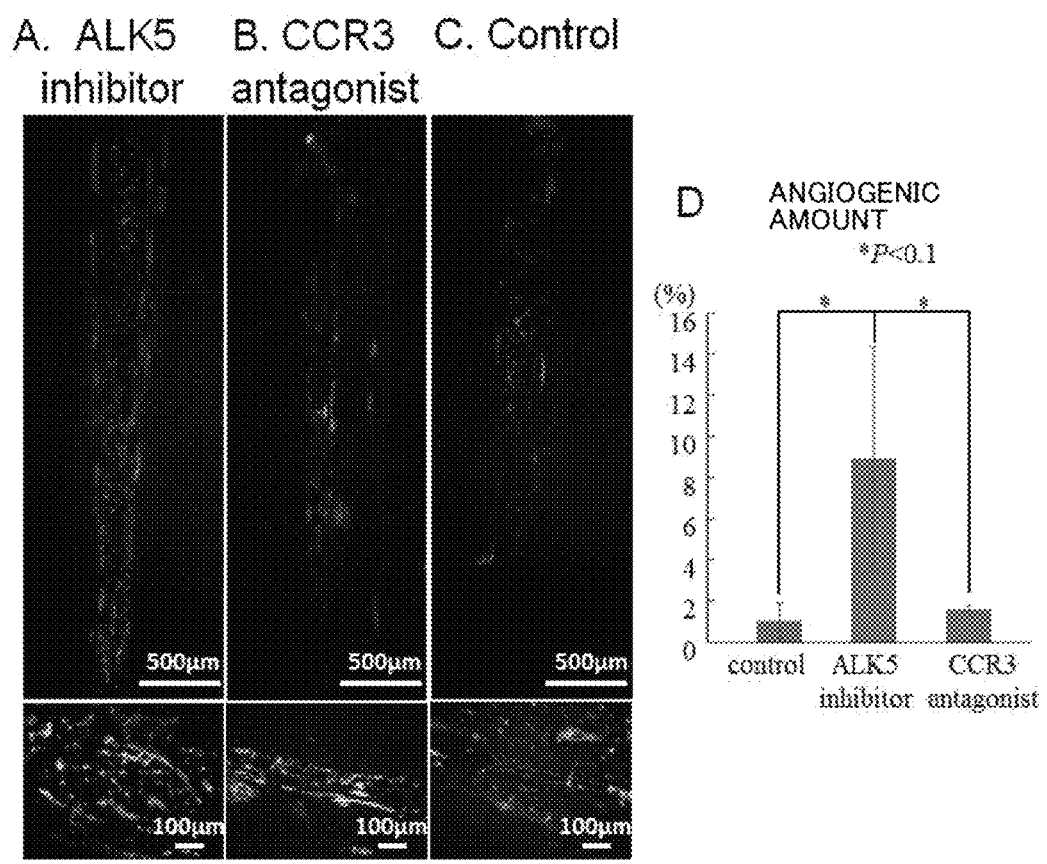
Figure 12:
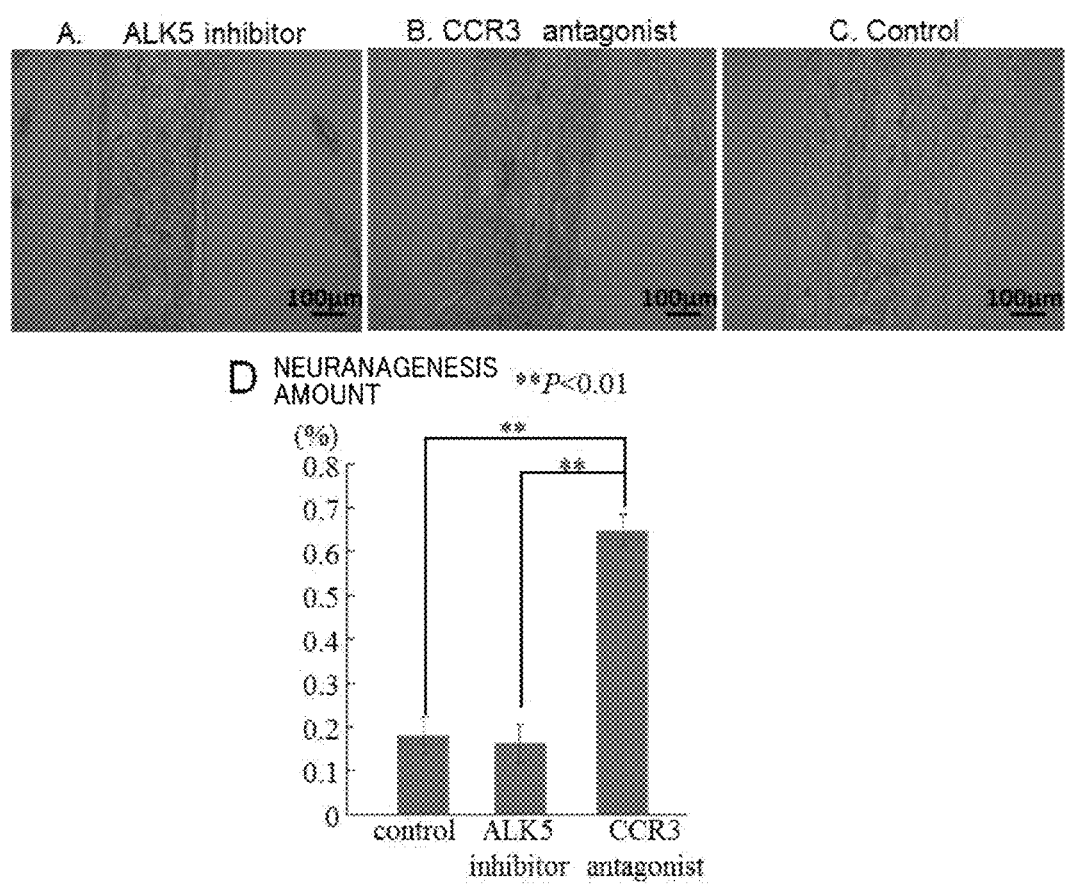

The injection of the root canal filler containing the ALK5 inhibitor or the CCR3 antagonist into the post-pulpectomy root canal of a tooth of the canine of middle or advanced age resulted in a significant increase in the amount of regenerated dental pulp tissue after 14 days and 60 days, as compared to the case of the root canal filler not containing the ALK5 inhibitor or the CCR3 antagonist (FIGS. 9 and 10). Application of the ALK5 inhibitor or the CCR3 antagonist produced the following results. After 60 days, the injection of the root canal filler containing the ALK5 inhibitor caused a significant increase in density of angiogenesis (FIG. 11), as compared to the case of the root canal fillers containing no ALK5 inhibitor (see Graph D in FIG. 11, the graph showing the angiogenic amount). The injection of the root canal filler containing the CCR3 antagonist caused a significant increase in neurite outgrowth (FIG. 12) after 60 days, as compared to the case of the root canal fillers containing no CCR3 antagonist (see Graph D in FIG. 12, the graph showing the neurogenic amount).

Figure 13:
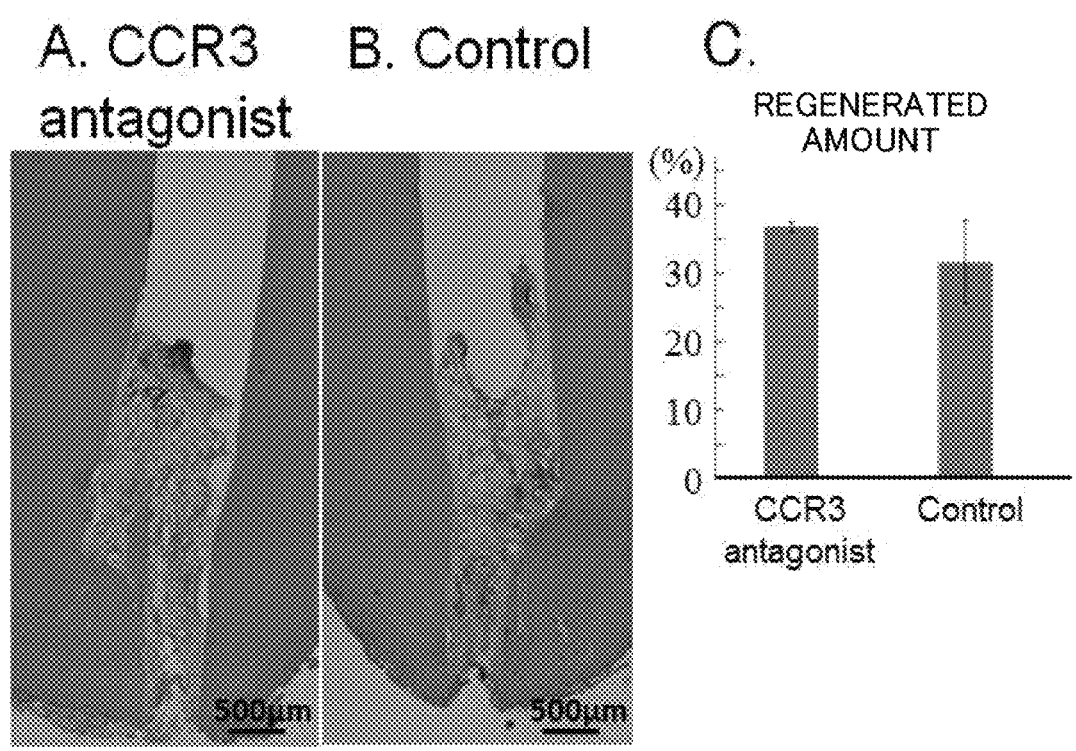

The injection of the root canal filler containing the CCR3 antagonist into the post-pulpectomy root canal of a tooth of the canine of young age did not cause any significant increase in the amount of regenerated dental pulp tissue after 14 days, as compared to the case of the root canal filler containing no CCR3 antagonist (FIG. 13). Thus, it has been revealed that the CCR3 antagonist is particularly effective for an individual of middle or advanced age, which is a concept encompassing both an individual of middle age and an individual of advanced age (see Graph C in FIG. 13, the graph showing the amount of regenerated dental pulp tissue). It has also been revealed that the ALK5 inhibitor is particularly effective for an individual of middle or advanced age. The following examples will reveal further that the CCR3 antagonist, the ALK5 inhibitor, and a CCL11-neutralizing antibody are particularly effective for an individual of middle or advanced age.

Example 4

(Dental Pulp Regeneration after Pulpectomy in a Case of Transplantation of Root Canal Filler Containing ALK5 Inhibitor or CCR3 Antagonist Together with Allogeneic Dental Pulp Stem Cells after Pretreatment with Trypsin into Middle or Advanced Aged Dogs)

After 7 to 14 days following a pulpectomy treatment, the treated root canal underwent alternate washing, and then, washing with physiologic saline. Smear clean was then allowed to react for 2 minutes. The root canal was then further washed with physiologic saline, and dried. Further, FRANCETIN•T•POWDER (2,500 USP of crystalized trypsin per 10 mg) (MOCHIDA PHARMACEUTICAL CO., LTD.) was mixed with a nanobubble liquid into a 50 µg/ml (0.05%) solution. The solution was allowed to react for 10 minutes. The root canal was washed with physiologic saline, and dried. In the same manner as in Example 3, a root canal filler was prepared by suspending 1×10$^6$ allogeneic dental pulp stem cells, which had been membrane-isolated, in 40 µl of a scaffold (Koken Atelocollagen Implant), and by suspending 3 µl of a 100 µg/ml G-CSF (NEUTROGIN). Further a CCR3 antagonist (SB328437, 200 ng) was added to the root canal filler. The root canal filler was injected into the post-pulpectomy root canal. After 14 days following the transplantation, the tooth was extracted, and 5 µm paraffin sections were prepared. The paraffin sections were then H-E stained to undergo morphological observation.

tems 7500 Real-time PCR system (Applied Biosystems). Reaction conditions of Real-time RT-PCR were set as one cycle of 95° C. for 15 seconds and 65° C. for 1 minute, and 40 cycles were carried out. The nucleotide sequences of the primers used are shown in the table below. The mRNA expression of the amplified genes was corrected with β-actin mRNA.

TABLE 2

Table: Human Primer Real-time RT-PCR

| Gene | | 5'←DNA Sequence→3' | Product size | Accession number |
|---|---|---|---|---|
| β-actin | Forward 5'-1 | GGACTTCGAGCAAGAGATGG | 234 bp | NM_001101 |
| | Reverse 3'-2 | AGCACTGTGTTGGCGTACAG | | |
| p16 | Forward 5'-3 | GAA GGT CCC TCA GAC ATC CCC | 94 bp | NM_000077 |
| | Reverse 3'-4 | CCC TGT AGG ACC TTC GGT GAC | | |
| CCL11 | Forward 5'-3 | TTCTGTGGCTGCTGCTCATAG | 125 bp | NM_002986 |
| | Reverse 3'-6 | GCTCTCTAGTCGCTGAAGGG | | |
| CCR3 | Forward 5'-1 | CTGTACTCCCTGGTGTTCACTG | 109 bp | NM_001837 |
| | Reverse 3'-2 | GGTTGAGCAGGTAGATGTTGG | | |

Figure 14:
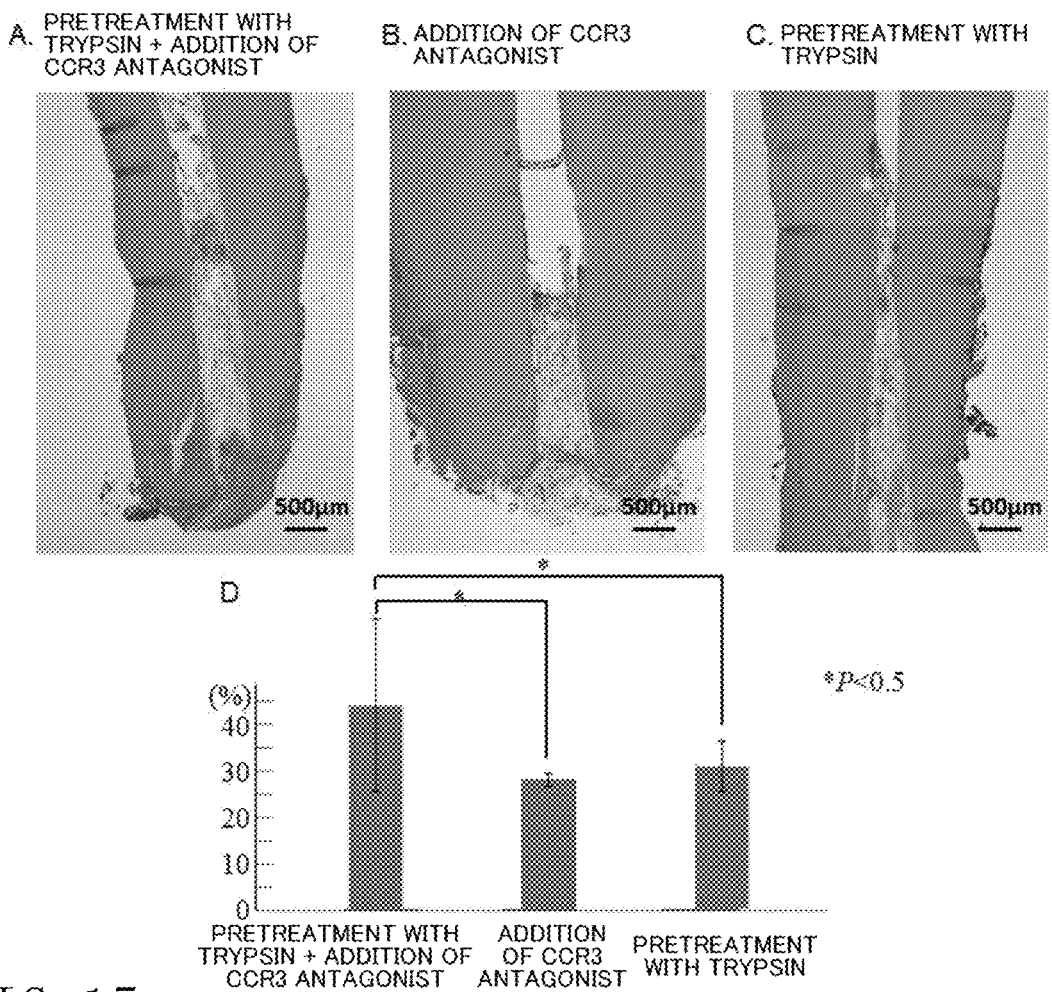
FIG. 14 includes photographs that show morphological observation, 14 days after transplantation of allogeneic dental pulp stem cells into a dog tooth middle or advanced age. Specifically, Photograph A shows a tooth into which a CCR3 antagonist (SB328437, 200 ng) was transplanted together with dental pulp stem cells, G-CSF, and collagen, after a pretreatment with trypsin. Photograph B shows a tooth into which a CCR3 antagonist (SB328437, 200 ng) was transplanted together with dental pulp stem cells, G-CSF, and collagen, without pretreatment with trypsin. Photograph C shows a control into which only dental pulp stem cells, G-CSF, and collagen were transplanted according to a common method, after a pretreatment with trypsin. Graph D shows a statistical comparison of the amounts of regenerated dental pulp.

Following a pretreatment with trypsin, the injection of the root canal filler containing the CCR3 antagonist into the post-pulpectomy root canal of a tooth of the canine of middle or advanced age resulted in a significant increase in the amount of regenerated dental pulp tissue after 14 days, as compared to the case where no pretreatment was performed (FIG. 14). Thus, it is presumed that a combination of the ALK5 inhibitor or the CCR3 antagonist with trypsin provides an additive effect.

Example 5

(Effects of CCL11-Neutralizing Antibody and CCR3 Antagonist in Dental Pulp Stem Cells of Human of Middle or Advanced Age)

1. Culture of Dental Pulp Stem Cells

Dental pulp was extracted from the third molar of each of elderly persons (60 years and 70 years of age, respectively) and young persons (19 years and 26 years of age, respectively) with the consent of these persons. The dental pulp was cut into small pieces in Hanks solution. The small pieces underwent enzymatic digestion with a 0.04 mg/ml liberase solution (Roche diagnostics, Pleasanton, Calif., USA) at 37° C. for 1 hour, so that dental pulp cells were separated. The dental pulp cells were plated in DMEM (D 6429) containing 10% human serum (Sigma-Aldrich, St. Louis, Mo., USA) in 35 mm dishes at a cell concentration from $2 \times 10^4$/ml to $4 \times 10^4$/ml. Thereafter, while the medium was replaced every 2 to 3 days, the cells were subcultured when reaching 70% confluence. For cell detachment, TrypLE™ Select (Life Technologies, Carlsbad, Calif., USA) was used.

2. Real-time RT-PCR

Total RNA was extracted from various cells using Trizol (Life Technologies). After a treatment with DNase (Roche diagnostics), First-strand cDNA was synthesized using ReverTra Aceα (TOYOBO, Tokyo, Japan). Real-time RT-PCR was performed on CCL11 mRNA by use of PowerUp SYBR™ Green master mix (Applied Biosystems, Foster City, Calif., USA), and on other genes by use of Power SYBR' Green master mix (Applied Biosystems). Amplification and detection were carried out using Applied Biosys- 3. Analysis of Changes in CCL11 Protein Expression of Dental Pulp Stem Cells Caused by Treatment with CCL11-Neutralizing Antibody After removal of supernatant of the cells, a part of the cells were washed several times with PBS(−). In the absence of serum, the medium was replaced with DMEM containing a CCL11-neutralizing antibody (anti-CCL11/Eotaxin antibody) (MAB320, R&D systems, Minneapolis, Minn., USA) (dissolved in 5% Trehalose-PBS, a stock concentration of 500 µg/ml). Specifically, the DMEM was added to achieve a final concentration of 10 µg/ml. The cells were then cultured for 48 hours. As a vehicle control, another part of the cells were cultured for 48 hours in DMEM containing 0.1% Trehalose-PBS. The stock concentration of the CCL11-neutralizing antibody was 500 µg/ml. Since a final concentration of 10 µg/ml is achieved by addition of trehalose to a culture solution at 0.1%, the Trehalose-PBS was added to achieve a concentration of 0.1%. Thereafter, following removal of the culture solution, the cells were washed with PBS(−). The cells were dissolved in nonreducing 1× Sample Buffer (containing no (3-mercaptoethanol), heated at 95° C. for 5 minutes, thereby preparing samples. The samples were used after measurement of protein concentration by BCA.

Electrophoresis was carried out using 12% TGX™ FastCast™ Acrylamide Kit (BIO-RAD, Hercules, Calif., USA). Blotting was carried out on PVDF membrane (Millipore, Billerica, Mass., USA) using a semi-dry type blotting apparatus (BIO-RAD). The membrane was blocked with κ% skim milk-PBS+0.05% Tween 20. CCL11-neutralizing antibody (anti-CCL11/Eotaxin antibody; MAB 320, R&D systems) (1:500), as a primary antibody, was allowed to react overnight at 4° C. Further, anti-mouse IgG-HRP linked antibody (Cell Signaling, Beverly, Mass., USA) (1; 1,000), as a secondary antibody, was allowed to react at 4° C. for 2 hours. Thereafter, chemiluminescence was produced with Luminata™ Forte Western HRP Substrate (Millipore). Bands were detected using Light-Capture II cooled CCD camera system (Atto Corp., Tokyo, Japan). Expression of β-actin was examined as an internal control. To detect β-actin, a necessary amount of β-mercaptoethanol was added to the prepared nonreducing sample, and the sample was heated at 95° C. for 5 minutes, to be used as the sample. The process from the electrophoresis to the blocking was carried out in the same manner. As a primary antibody, anti-β-actin antibody (RB-9421, NeoMarkers, Fremont, Calif., USA) (1:1,000) was allowed to react overnight at 4° C. Anti-rabbit IgG-HRP linked antibody (Cell Signaling) was used as a secondary antibody. Chemiluminescence and band detection were carried out in the same manner.

Figure 15:
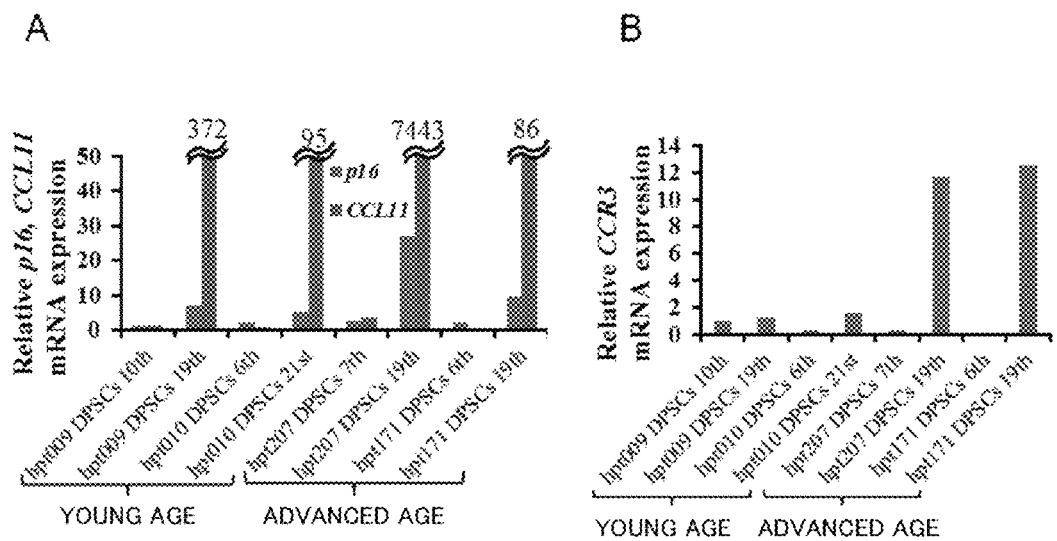
FIG. 15 shows a relationship between cell senescence and expression of CCL11 and a relationship between cell senescence and expression of CCR3 in human dental pulp stem cells. Graph A shows that dental pulp stem cells of a human of young age and those of a human of middle or advanced age both exhibited an increase in mRNA expression of p16 and an increase in mRNA expression of CCL11 due to long-term passage. That is, it is suggested that CCL11 expression may increase due to senescence. Graph B shows that mRNA expression of CCR3 which is a receptor of CCL11 increases in long-term passage of human dental pulp stem cells at middle or advanced age, whereas such an increase in mRNA expression of CCR3 is not observed in long-term passage of human dental pulp stem cells at young age. Note that "ADVANCED AGE" in these graphs stands for middle or advanced age. The same applies in the following.

It has been found that p16 mRNA expression increases with increase in the passage number, and CCL11 mRNA expression also increases with increase in p16 mRNA expression (Graph A in FIG. 15). This suggests that CCL11 is associated with cell senescence. In view of a report that in cells derived from an individual of middle or advanced age, an increase in the expression of CCR3 that is a receptor of CCL11 enhances the sensitivity (Wang H et al., Invest Ophthalmol Vis Sci. 2011), changes in CCR3 mRNA expression associated with long-term passage were also analyzed by real-time RT-PCR. As a result, there was no correlation between the age of donor and CCR3 mRNA expression in the case of short-term passage (6th to 10th) (data not shown). On the other hand, CCR3 mRNA expression increased in the case of long-term passage (19th to 21st) at any age (Graph B in FIG. 15).

4. Analysis of Changes in In-Vitro Migratory Capacity of Dental Pulp Stem Cells Caused by Pretreatment with CCL11-Neutralizing Antibody It was investigated whether migratory capacity with respect to culture supernatant of dental pulp stem cells changed by addition of a CCL11-neutralizing antibody to long-term passage dental pulp stem cells in the absence of serum.

The culture supernatant of dental pulp stem cells was prepared in the following manner: A culture solution was removed from cultured dental pulp stem cells of a human of young age (30 years old). The cells were washed several times with PBS(-). After the medium was replaced with serum-free DMEM, the cells were cultured for 24 hours. The supernatant was collected, from which cell components were removed by centrifugation. The supernatant was then centrifugally concentrated approximately 50-fold with Amicon Ultra-15 Centrifugal Filter Unit (Millipore). The protein concentration was measured by the Bradford method. The culture supernatant was then used.

Long-term passage dental pulp stem cells of an individual of young age (hpt009 DPSCs 19th) were provided. A part of the dental pulp stem cells prepared were cultured for 48 hours with a CCL11-neutralizing antibody (at a final concentration of 10 μg/ml) in the absence of serum. Another part of the dental pulp stem cells prepared were cultured with DMEM containing 0.1% Trehalose-PBS as vehicle for 48 hours in the absence of serum. Thereafter, the cells were detached and the migratory capacity with respect to the culture supernatant of the dental pulp stem cells was analyzed using TAXIScan-FL (Effector Cell Institute, Tokyo). Specifically, 1 μl of the cells ($10^5$ cells/ml) was injected to one end portion of a channel optimized for the size of the cell (8 mm) and interposed between a silicon plate having 6 μm pores and a glass plate. To the opposite end portion, 4.5 μg of the culture supernatant of the dental pulp stem cells was placed such that a concentration gradient was formed. Based on the video images, the number of migrating cells was measured every 3 hours up to 24 hours.

Figure 16:
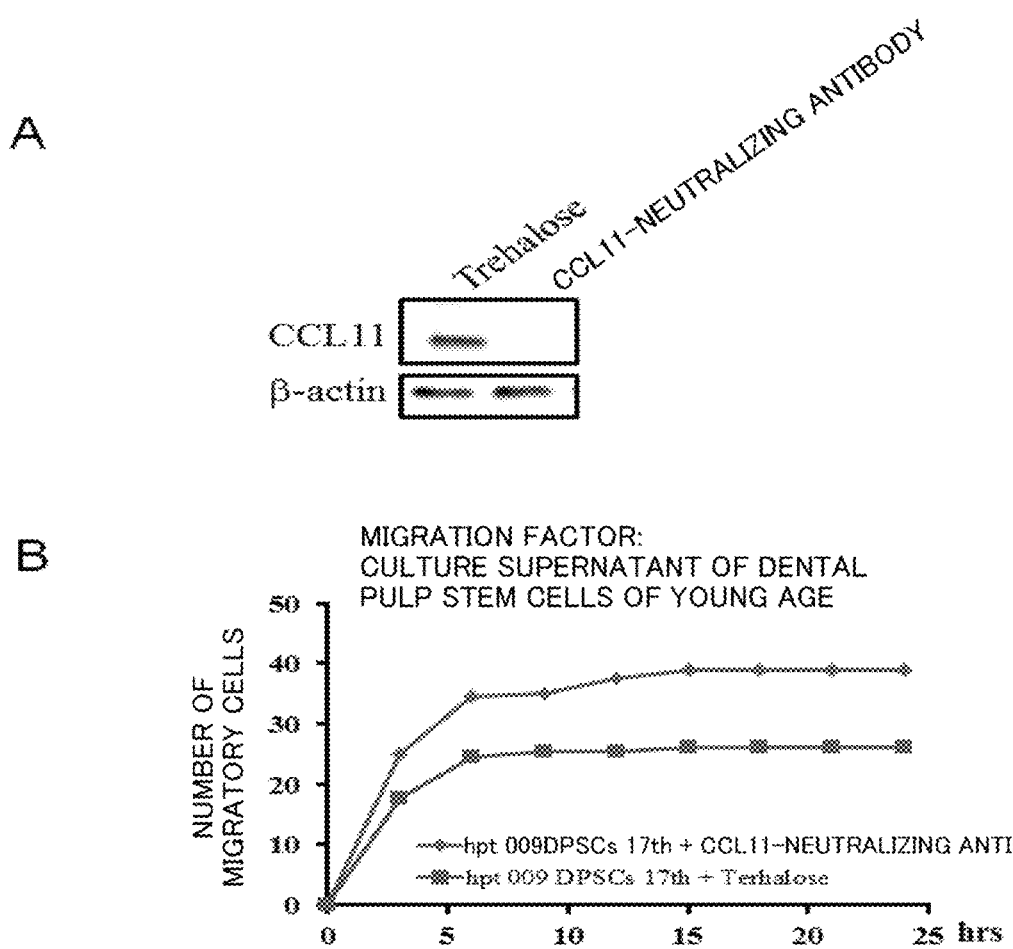
FIG. 16 includes Image A and Graph B. Image A shows loss of CCL11 expression by addition of a CCL11-neutralizing antibody to dental pulp stem cells expressing CCL11. Graph B shows effect of a CCL11-neutralizing antibody on the migratory capacity of long-term passage of human dental pulp stem cells at young age. Migratory capacity is lowered by long-term passage, but addition of the CCL11-neutralizing antibody increases migratory capacity.

The results show that pretreating dental pulp stem cells with a CCL11-neutralizing antibody causes a decrease in the expression of CCL11 protein (Image A in FIG. 16).

Next, following a pretreatment with the CCL11-neutralizing antibody lasting 48 hours in the absence of serum, the migratory capacity was analyzed. An analysis of long-term passage dental pulp stem cells derived from a human of middle or advanced age turned out to be difficult because the number of migrating cells themselves was very small. Accordingly, long-term passage dental pulp stem cells derived from a human of young age were analyzed. As a result, the migratory capacity of the cells precultured with the CCL11-neutralizing antibody was higher than that of the cells precultured with trehalose (Graph B in FIG. 16).

Example 6

(Effect of CCL11-Neutralizing Antibody in Ectopic Dental Pulp Regeneration Model of Middle or Advanced Aged Mouse)

1. Continuous Infusion of CCL11-Neutralizing Antibody by Osmotic Pump in Ectopic Transplantation Mouse Model An anterior teeth (mandibular lateral incisors) extracted from of pigs were each cut to a width of 6 mm, and the root canal was expanded to 2 mm. Thereafter, one side of the root canal was sealed with zinc phosphate cement, thereby preparing grafts. Collagen TE (Nitta collagen) and $5 \times 10^5$ cells of membrane-separated porcine dental pulp cells were injected into each graft. After incubated at 37° C., the grafts were transplanted subcutaneously in the abdomen of SCID mice (CLEA Japan, Inc.), including 4 mice of young age (5 weeks old) and 4 mice of middle or advanced age (40 to 50 weeks old) each under deep anesthesia. At the same time, 50 μg/kg of a CCL11-neutralizing antibody (R&D systems) or 20 μg/ml of trehalose was continuously administered subcutaneously to the dorsum by an osmotic pump (ALZET) each day.

After 21 days following the transplantation, the mice were reflux-fixed with 4% paraformaldehyde (PFA) under deep anesthesia, and the grafts were collected. The grafts were immersed and fixed in PFA for 24 hours, and decalcified with Kalkitox (WAKO) for 7 days. Paraffin sections with a thickness of 5 μm were obtained from the grafts. First, in order to compare amounts of regenerated tissues, the sections were stained with HE and observed with an optical microscope to measure an amount of regenerated dental pulp with respect to the area of the root canal. Furthermore, in order to compare calcified areas of the regenerated tissues, the sections were stained with Masson Trichrome and observed with an optical microscope. The calcified area in the regenerated dental pulp was measured. In order to compare densities of angiogenesis, the sections were subjected to fluorescence tissue immunostaining with lectin (Vector) and observed with an optical microscope to measure an area of regenerated tissue and an area of new blood vessels.

2. Comparison of Blood Levels of CCL11

Using an animal lancet (BioResearch), 500 μl of blood was collected from the mice of middle or advanced age and the mice of young age before and after the surgery. Thereafter, blood levels of CCL11 were measured and compared by ELISA.

Figure 17:
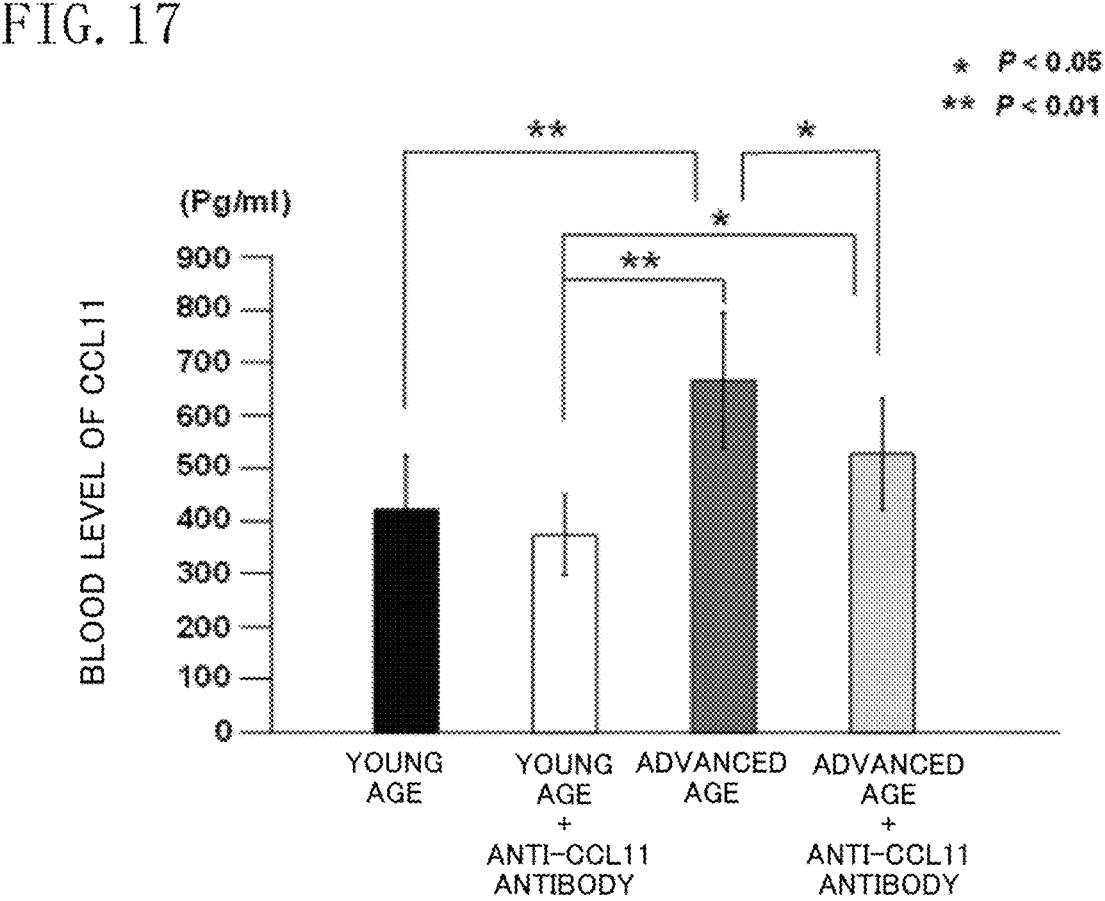
FIG. 17 shows blood levels of CCL11 in mice of young age and mice of middle or advanced age. In the mice of middle or advanced age, administration of a CCL11-neutralizing antibody significantly reduces the blood level of CCL11. *P<0.05, **P<0.01

FIG. 17 shows the results of the comparison of the blood levels of CCL11. Before the surgery, the mice of middle or advanced age were significantly higher in the blood levels of CCL11 than the mice of young age, whereas on day 21 after the surgery, no difference was observed.

Figure 18:
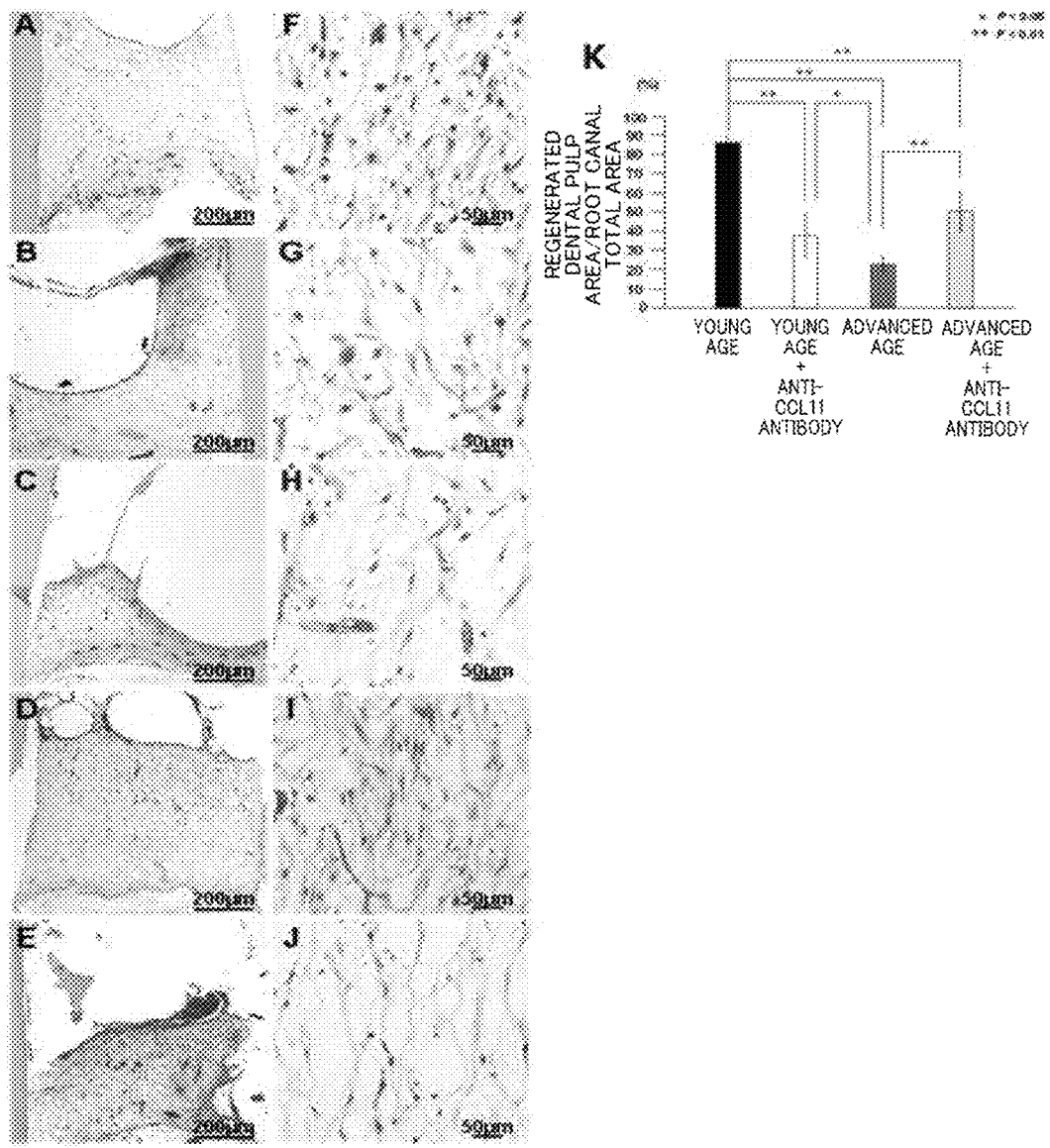
FIG. 18 shows effect of administration of a CCL11-neutralizing antibody in promoting dental pulp regeneration in mice of middle or advanced age into ectopic tooth transplantation model. Photographs A, B, F, and G are HE images of the regenerated dental pulp of the mice of young age 21 days after the transplantation into ectopic tooth transplantation model. Photographs C to E and H to J are HE images of the regenerated dental pulp of the mice of middle or advanced age after 21 days after the transplantation into ectopic tooth transplantation model. Photographs B, G, D, and I show the result of continuous administration of a CCL11-neutralizing antibody carried out in combination with infusion of dental pulp stem cells at the time of the ectopic transplantation. Photographs E and J show the result of continuous administration of trehalose carried out in combination with infusion of dental pulp stem cells at the time of the ectopic transplantation. Photographs A, F, C, and H show the controls that received transplantation of dental pulp stem cells alone. Graph K is shows a comparison of amounts of regeneration (regenerated dental pulp area/root canal total area). *P<0.05, **P<0.01

FIG. 18 shows the result of analysis of changes in regeneration amount in the mouse models of ectopic transplantation that received continuous infusion of CCL11- neutralizing antibody by osmotic pump. The amount of regenerated dental pulp of the mice of middle or advanced age was significantly lower than that of the mice of young age (Photographs A and C in FIG. 18). Further, the regenerated dental pulp of the mice of middle or advanced age showed calcification or inflammation, whereas such findings were not observed in the regenerated dental pulp of the mice of young age. The continuous administration of CCL11-neutralizing antibody caused a significant increase in the amount of regenerated dental pulp of the mice of middle or advanced age, as compared to the non-administered group. (Photographs C, D, and Graph K in FIG. 18). A comparison of the mice of young age shows that the amount of regenerated dental pulp of the administered group is significantly smaller than that of the non-administered group (Photographs A, B, and Graph K in FIG. 18). In addition, even though the continuous administration of trehalose, which is a buffer for antibody, was carried out by osmotic pump, there was no difference in the amount of regenerated dental pulp in both of the mice of young age and the mice of middle or advanced age (Photograph E in FIG. 18).

Figure 19:
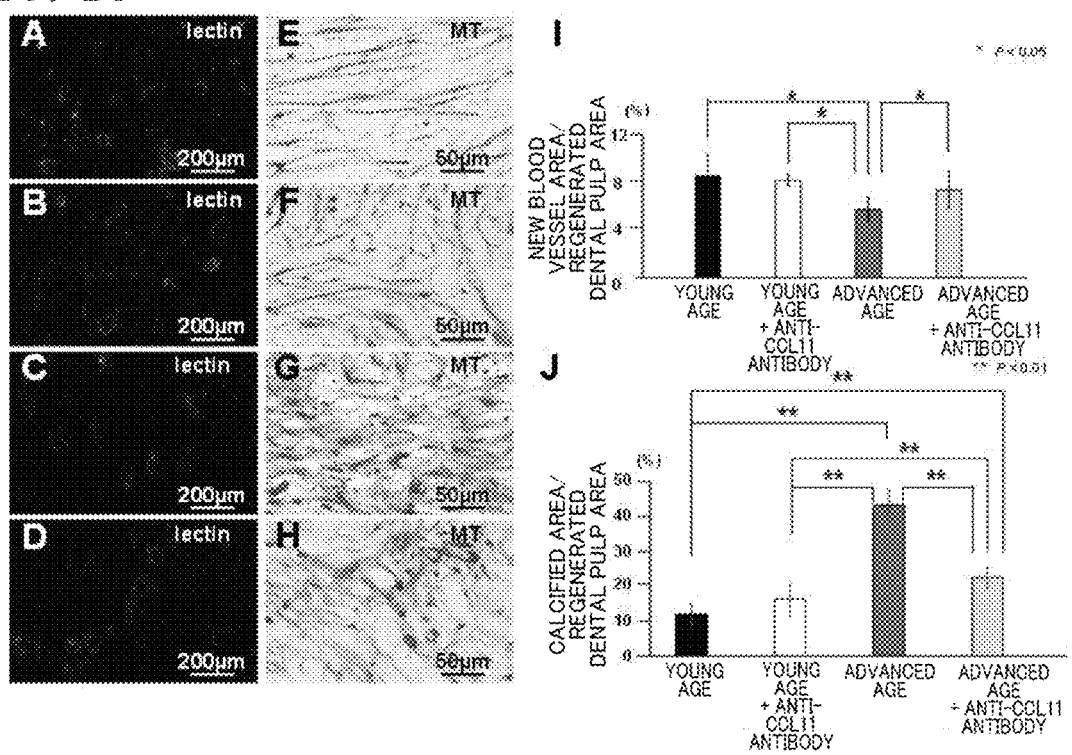
FIG. 19 shows that administration of a CCL11-neutralizing antibody caused an increase in density of new blood vessels and a decrease in calcified amount in dental pulp regenerated in mice of middle or advanced age into ectopic tooth transplantation model. Photographs A, B, E, and F show the results of dental pulp regeneration in mice of young age after the transplantation into ectopic tooth transplantation model. Photographs C, D, G and H show the result of dental pulp regeneration in mice of middle or advanced age after the transplantation of ectopic radix dentis. Photographs B, F, D, and H show the result of continuous administration of a CCL11-neutralizing antibody carried out at the time of the ectopic transplantation. Photographs A to D are lectin stain images. Photographs E to H D are Masson trichrome (MT) stain images. Graph I shows a comparison of new blood vessel area of mice of young age and that of mice of middle or advanced age, and Graph J shows a comparison of a calcified area of the mice of young age and that of the mice of middle or advanced age. *P<0.05, **P<0.01

FIG. 19 shows the result of analysis of changes in the angiogenic density and the calcified area before and after the administration. As to the dental pulp regeneration of mice of middle or advanced age by transplantation, the group received the continuous administration of CCL11-neutralizing antibody showed a significant increase in density of new blood vessels as compared to the non-administered group, so that there was no significant difference in the density between the mice of middle or advanced age and the mice of young age (Photographs A to D and Graph I in FIG. 19). Furthermore, though the calcification and inflammation, which were observed in the non-administered group, were reduced, the calcified area of the administered group of the mice of middle or advanced age was significantly different from the calcified area in the regenerated dental pulp of the transplanted group of the mice of young age (Photographs E to H, and Graph J in FIG. 19). On the other hand, a comparison of the mice of young age before and after the administration shows no significant difference in the angiogenic density and the calcified area.

3. Number of M1 and M2 Macrophage Cells and M1/M2 Rate in Regenerated Dental Pulp An anterior teeth (mandibular lateral incisors) extracted from of pigs was cut to a width of 6 mm, and the root canal was expanded to 2 mm. Thereafter, one side of the root canal was sealed with zinc phosphate cement, thereby preparing grafts. Collagen TE (Nitta collagen) and membrane-separated porcine dental pulp cells were injected into each graft. After incubated at 37° C., the grafts were transplanted subcutaneously in the abdomen of SCID mice (CLEA Japan, Inc.), including of 4 mice of young age (5 weeks old) and 4 mice of middle or advanced age (40 to 50 weeks old) each under deep anesthesia. At the same time, 50 µg/kg of CCL11-neutralizing antibody (R&D systems) or 20 µg/ml of trehalose was continuously administered subcutaneously to the dorsum by an osmotic pump (ALZET) each day.

On day 7 after the transplantation, the grafts were collected and fixed in PFA. After decalcification, paraffin sections with a thickness of 5 µm were prepared. For each section, CD68 (abcam) and CD11c (abcam) as M1 macrophage markers and CD68 and CD206 (abcam) as M2 macrophage markers were immunostained. Further, M1/M2 rates were calculated and compared.

Figure 20:
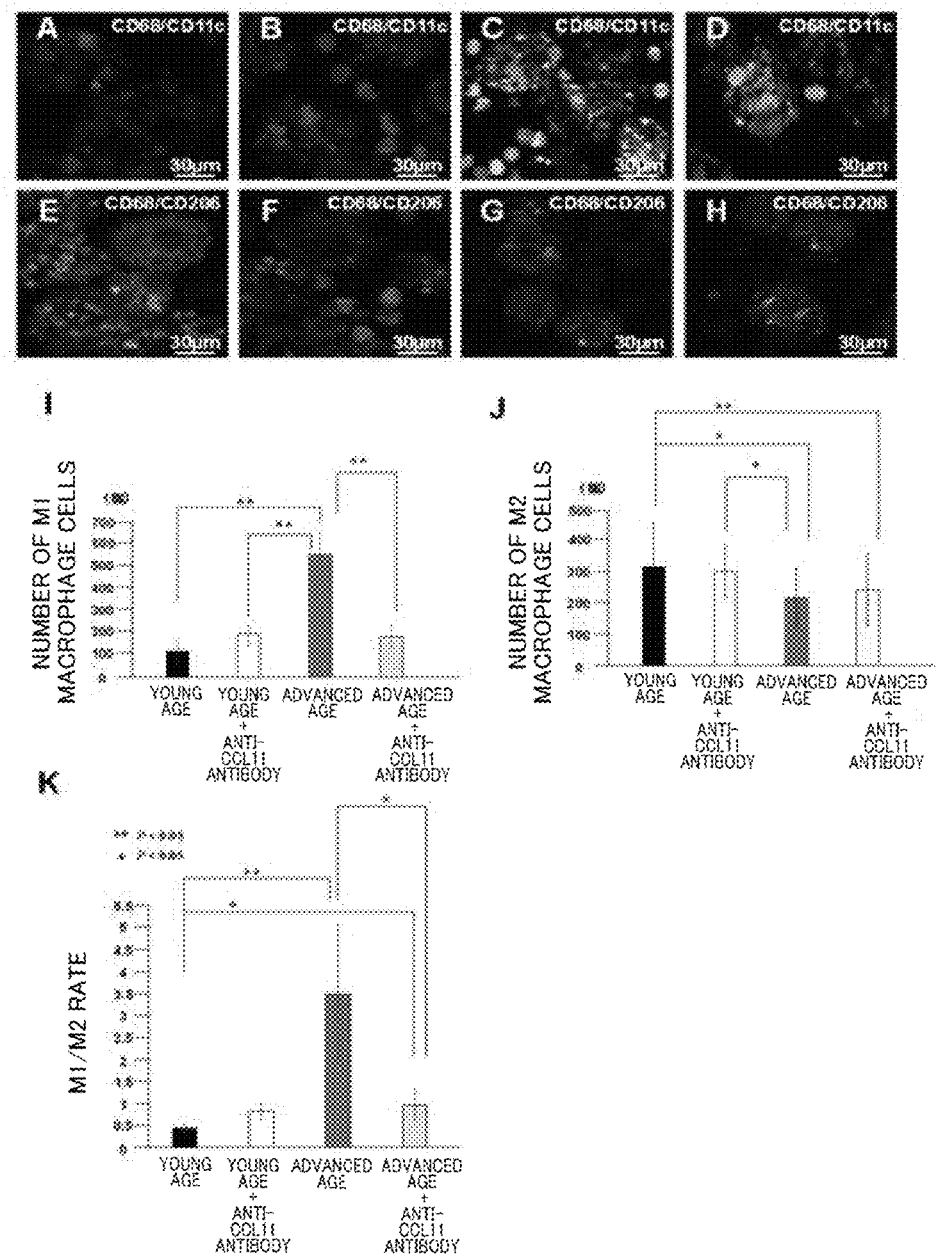
FIG. 20 shows changes in the number of M1 macrophages, the number of M2 macrophages, and an M1/M2 rate caused by administration of a CCL11-neutralizing antibody in regenerated dental pulp in mice into which ectopic radix dentis was transplanted. In the regenerated dental pulp in the mice of middle or advanced age into which ectopic radix dentis was transplanted, the administration of the CCL11-neutralizing antibody significantly reduced the number of M1 macrophages and the M1/M2 rate. Photographs A, B, E, and F show the results of dental pulp regeneration in mice of young age after the transplantation of ectopic radix dentis. Photographs C, D, G and H show the result of dental pulp regeneration in mice of middle or advanced age after the transplantation of ectopic radix dentis. Photographs B, D, F, and H show the groups that underwent continuous administration of the CCL11-neutralizing antibody. Photographs A to D are double immunohistological stain images of regenerated dental pulp, the images showing CD68 and CD11c (green: CD68, red: CD11c). Photographs E to H are double immunohistological stain images of regenerated dental pulp, the images showing CD68 and CD206 (green: CD68, red: CD206). Graph I shows the numbers of M1 macrophages in regenerated dental pulp. Graph J shows the numbers of M2 macrophages in regenerated dental pulp. Graph K shows M1/M2 rates. *P<0.05, **P<0.01 (The data represent the average±standard deviation of four tests.)

The results show that for the dental pulp regeneration models with radix dentis ectopic transplantation, many M1 macrophage cells positive for CD68/CD11c were found in the regenerated dental pulp of the mice of middle or advanced age while a reduced number of positive cells were found in the group received the continuous administration of CCL11-neutralizing antibody (Photographs C, D and Graph I in FIG. 20). In addition, the number of M2 macrophage cells positive for CD68/CD206 (mannose receptor) did not differ greatly between the non-administration group and the administered group (Photographs G, H and Graph J in FIG. 20). On the other hand, for the mice of young age, the non-administration group and the administered group showed a smaller number of M1 macrophages than that of the mice of middle or advanced age. The number of M2 macrophage cells was large in both the non-administration group and the administered group (Photographs A, B, E, F and Graphs I, J in FIG. 20). Next, the M1/M2 rate of the regenerated dental pulp after the continuous administration of a CCL11-neutralizing antibody and the M1/M2 rate of the regenerated dental pulp not having received administration of the CCL11-neutralizing antibody were measured and compared. The result shows that the regenerated dental pulp of the administered mice of middle or advanced age has a reduced M1/M2 rate (Graph K in FIG. 20). Thus, it can be said that the administration of CCL11-neutralizing antibody reduces inflammatory reaction in the regenerated dental pulp of the mice of middle or advanced age, creating an environment that is likely to promote regeneration and repair reaction.

Example 7

(Effects of ALK5 Inhibitor and CCR3 Antagonist in Senescent Cells of Human Periodontal Membrane)

1. Changes in mRNA Expression of CCL11, CCR3, and GDF11 in Human Periodontal Membrane Cells Caused by Addition of ALK5 Inhibitor and CCR3 Antagonist Fifth-passage human periodontal membrane cells were plated in a DMEM containing 10% FBS in collagen-coated 35 mm dishes (IWAKI) at a density of $2 \times 10^4$ cells/ml. After 9 hours, an ALK5 inhibitor (SB431542) was added to final concentrations of 5 ng/µl, 10 ng/µl, and 30 ng/µl. Further, a CCR3 antagonist (SB328437) was added to final concentrations of 5 ng/µl, 10 ng/µl, and 30 ng/µl. After 32 hours, mRNA was extracted, and real-time RT-PCR was performed on CCL11, CCR3, and GDF11.

TABLE 3

Table: Human Primer Real-time RT-PCR

| Gene | | 5'←DNA Sequence→3' | Product size | Accession number |
|---|---|---|---|---|
| GDF11 | Forward 5'-1 | CAAGTCGCAGATCTTGAGCA | 490 bp | NM_005811.4 |
| | Reverse 3'-2 | CACTTGCTTGAAGTCGATGC | | |
| CCL11 | Forward 5'-3 | TTCTGTGGCTGCTGCTCATAG | 125 bp | NM_002986 |
| | Reverse 3'-6 | GCTCTCTAGTCGCTGAAGGG | | |
| CCR3 | Forward 5'-1 | CTGTACTCCCTGGTGTTCACTG | 109 bp | NM_001837 |
| | Reverse 3'-2 | GGTTGAGCAGGTAGATGTTGG | | |

The result shows that mRNA expression of CCL11 was completely suppressed by the ALK5 inhibitor (SB431542) and the CCR3 antagonist (SB328437). As a result, mRNA expression of CCR3 was completely suppressed by the CCR3 antagonist (SB328437). In addition, the ALK5 inhibitor increased the expression of GDF11 mRNA by 5 times.

2. Changes in Expression of Senescence Marker in Senescent Cells of Human Periodontal Membrane Caused by Addition of ALK5 Inhibitor and CCR3 Antagonist Eleventh-passage human periodontal ligament cells were plated in DMEM containing 10% FBS in collagen-coated 35 mm dishes (IWAKI) at a density of $2 \times 10^4$ cells/ml. After 20 hours, ALK5 inhibitor (SB431542) was added to final concentrations of 5 ng/μl and 10 ng/μl. Further, CCR3 antagonist (SB328437) was added to final concentrations of 5 ng/μl and 10 ng/μl. After 48 hours, mRNA was extracted, and real-time RT-PCR was performed on senescence markers, namely p16, p53, IL6, IL1b, IL8, and TNFα (Table 4).

TABLE 4

Table: Human Primer Real-time RT-PCR

| Gene | | 5'←DNA Sequence→3' | Product size | Accession number |
|---|---|---|---|---|
| p16 | Forward 5'-1 | GAAGGTCCCTCAGACATCCCC | 94 bp | NM_000077 |
| | Reverse 3'-2 | CCCTGTAGGACCTTCGGTGAC | | |
| p53 | Forward 5'-3 | AGGCCTTGGAACTCAAGGAT | 85 bp | NM_000546.4 |
| | Reverse 3'-4 | CCCTTTTTGGACTTCAGGTG | | |
| IL6 | Forward 5'-3 | CCAGGAGCCCAGCTATGAAC | 64 bp | NM_000600 |
| | Reverse 3'-6 | CCCAGGGAGAAGGCAACTG | | |
| IL1β | Forward 5'-1 | GGCCCTAAACAGATGAAGTGCT | 62 bp | NM_000576 |
| | Reverse 3'-2 | TGCCGCCATCCAGAGG | | |
| IL8 | Forward 5'-1 | TTGGCAGCCTTCCTGATTTC | 65 bp | NM_000584 |
| | Reverse 3'-2 | TGCCGCCATCCAGAGG | | |
| TNFα | Forward 5'-1 | ACCAGGCCGTGATCTCTATG | 218 bp | AH003016 |
| | Reverse 3'-2 | TCCCTTTGTCCCTGGTCTC | | |

The result shows that the ALK5 inhibitor and the CCR3 antagonist significantly suppressed mRNA expression of the senescence markers of p16, IL6, IL1b, and IL8. In addition, the ALK5 inhibitor significantly suppressed TNFα mRNA expression (Table 5). Thus, it has been suggested that an ALK5 inhibitor and a CCR3 antagonist reduce senescence of senescent cells and restore the immunomodulation capacity of cells.

TABLE 5

Table: Senescence Marker Expression

| | ALK5 inhibitor | | CCR3 antagonist | | |
|---|---|---|---|---|---|
| | 5 ng/μl | 10 ng/μl | 5 ng/μl | 10 ng/μl | control |
| p16 | 0.36 | 0.10 | 0.14 | 0.30 | 1 |
| p53 | 0.92 | 0.50 | 0.56 | 0.92 | 1 |
| IL6 | 0.20 | 0.04 | 0.09 | 0.20 | 1 |
| IL1β | 0.16 | 0.03 | 0.09 | 0.31 | 1 |
| IL8 | 0.15 | 0.04 | 0.12 | 0.26 | 1 |

3. Changes in Trophic Factor Expression in Senescent Cells of Human Periodontal Membrane Caused by Addition of ALK5 Inhibitor and CCR3 Antagonist Real-time RT-PCR was performed on trophic factors, namely, VEGF, BDNF, NGF, MCP1 (Table below) using mRNA similar to that described in 2 above.

TABLE 6

Table: Human Primer Real-time RT-PCR

| Gene | | 5'←DNA Sequence→3' | Product size | Accession number |
|---|---|---|---|---|
| VEGF | Forward 5'-1 | GAA GGT CCC TCA GAC ATC CCC | 94 bp | NM_001033756 |
|  | Reverse 3'-2 | CCC TGT AGG ACC TTC GGT GAC | | |
| BDNF | Forward 5'-3 | AAACATCCGAGGACAAGGTG | 202 bp | NM_170735 |
|  | Reverse 3'-4 | CGTGTACAAGTCTGCGTCCT | | |
| NGF | Forward 5'-3 | ATACAGGCGGAACCACACTC | 181 bp | NM_002506 |
|  | Reverse 3'-6 | GCCTGGGGTCCACAGTAAT | | |
| MCP1 | Forward 5'-1 | GCCCCAGTCACCTGCTGTTA | 185 bp | NM_002982 |
|  | Reverse 3'-2 | TCCAGGTGGTCCATGGAATC | | |

The result shows that the ALK5 inhibitor and the CCR3 antagonist caused no significant change in the trophic factors expression (Table 6). Thus, it has been suggested that an ALK5 inhibitor and a CCR3 antagonist have no influence on expression of angiogenesis factors and neurotrophic factors with respect to senescent cells.

TABLE 7

Table: Trophic Factor Expression

| | ALK5 inhibitor | | CCR3 antagonist | | |
|---|---|---|---|---|---|
| | 5 ng/µl | 10 ng/µl | 5 ng/µl | 10 ng/µl | control |
| VEGF | 0.96 | 1.25 | 0.92 | 0.70 | 1 |
| BDNF | 0.44 | 0.47 | 0.33 | 0.43 | 1 |
| NGF | 0.58 | 0.44 | 0.50 | 0.58 | 1 |
| MCP1 | 1.08 | 0.96 | 2.35 | 0.54 | 1 |

4. Changes in Expression of Migratory Capacity-Related Factors in Senescent Cells of Human Periodontal Membrane of Caused by Addition of ALK5 Inhibitor and CCR3 Antagonist Real-time RT-PCR was performed on migratory capacity-related factors, namely, MMP9, MMP3, and MMP2 (Table 8) using mRNA similar to that described in 2 above.

TABLE 8

Table: Human Primer Real-time RT-PCR

| Gene | | 5'←DNA Sequence→3' | Product size | Accession number |
|---|---|---|---|---|
| MMP9 | Forward 5'-3 | TGGTGGTGATGGGCGTATCT | 87 bp | AF148064 |
|  | Reverse 3'-4 | CTGGCCATCACTGCTCAAAG | | |
| MMP3 | Forward 5'-3 | CCTCAGGAAGCTTGAACCTG | 192 bp | NM_002422 |
|  | Reverse 3'-6 | GGGAAACCTAGGGTGTGGAT | | |
| MMP2 | Forward 5'-1 | GACGGAAAGATGTGGTGTG | 191 bp | NM_001302510 |
|  | Reverse 3'-2 | AGACGGAAGTTCTTGGTGTAGG | | |

The result shows that the ALK5 inhibitor and the CCR3 antagonist reduced expression of the migration-related factor MMP9 (Table 9). Thus, it has been suggested that an ALK5 inhibitor and a CCR3 antagonist may reduce migratory capacity of senescent cells.

TABLE 9

Table: Trophic Factor Expression

| | ALK5 inhibitor | | CCR3 antagonist | | |
|---|---|---|---|---|---|
| | 5 ng/µl | 10 ng/µl | 5 ng/µl | 10 ng/µl | control |
| MMP9 | 0.10 | 0.06 | 0 | 0.63 | 1 |
| MMP3 | 1.08 | 0.96 | 2.34 | 0.54 | 1 |
| MMP2 | 0.93 | 1.02 | 0.54 | 0.75 | 1 |

5. Changes in Migratory Capacity in Senescent Cells of Human Periodontal Membrane Caused by Addition of ALK5 Inhibitor and CCR3 Antagonist Eleventh-passage human periodontal membrane cells were plated in DMEM containing 10% FBS in collagen-coated 35 mm dishes (IWAKI) at a density of $2\times10^4$ cells/ml. After 20 hours, an ALK5 inhibitor (SB431542) was added to a final concentration of 10 ng/µl. Further, a CCR3 antagonist (SB328437) was added to a final concentration of 5 ng/µl. After 48 hours, the cells were detached, and Real-time horizontal chemotaxis analysis was performed using TAXIscan-FL (Effector Cell Institute, Tokyo) so as to measure the migratory capacity. Specifically, channels optimized (8 µm) for the size of cells are formed between a silicon plate having 6 µm pores and a glass plate, and 1 µl of treated periodontal membrane cells ($10^5$ cells/ml) was injected to one end portion of an associated one of the channels (n=4). Then, 1 µl of 10 ng/µl SDF1 was placed on the opposite side portion so as to form a certain constant concentration gradient. Based on the video images of migration, the number of migrating cells after 12 hours was measured.

The result shows that the addition of the ALK5 inhibitor or the CCR3 antagonist significantly reduced the migratory capacity of the senescent cells of the periodontal membrane (Table 10).

TABLE 10

Changes in Migratory Capacity in Senescent Cells of Human Periodontal Membrane Caused by Addition of ALK5 Inhibitor and CCR3 Antagonist

|  | ALK5 Inhibitor | CCR3 antagonist | control |
|---|---|---|---|
| Average ± SD | 21.3 ± 10.9 | 23.3 ± 10.7 | 53.8 ± 4.6 |

Example 8

(Changes in Trophic Effect Caused by Addition of ALK5 Inhibitor and CCR3 Antagonist to Culture Conditioned Medium of Senescent Stem Cells of Human Dental Pulp)

1. Concentration of Culture Supernatant of Human Dental Pulp Stem Cells

Non-separated 22nd-passage human dental pulp stem cells were brought into a state of 50% confluence. The medium was replaced with a serum-free medium. After 24 hours, the culture conditioned medium was collected. The supernatant was concentrated approximately 40-fold using Amicon Ultra-15 Centrifugal Filter Unit with Ultracel-3 membrane (Millipore, Billerica, Mass.) with 3-kDa molecular cut. Proteinase inhibitors (Halt™ proteinase inhibitor cocktail EDTA-free, Thermo Scientific, Rockford, Ill., USA) was added. The mixture was dispended to be stored at −80° C. Protein content was measured using Bradford Ultra™ (Expedeon, Cambridge, UK).

2. Changes in Blood Vessel-Inducing Capacity Caused by Addition of ALK5 Inhibitor and CCR3 Antagonist to Culture Supernatant of Senescent Stem Cells of Human Dental Pulp HUVECs (Human Umbilical Vein Endothelial Cells) (clone 7F3415) (Lonza) were cultured with EGM 2 containing 10% FBS (Lonza). Thereafter, the culture supernatant (5 µg/ml proteins) prepared in 1 above was added to DMEM, as a blood vessel-inducing medium, containing 2% FBS, 5 µg/ml heparin (Lonza), 5 µg/ml ascorbic acid (Lonza), and 5 µg/ml hydrocortisone (Lonza). Further, an ALK5 inhibitor (SB431542, 10 ng/µl) was added to a part of the resultant mixture, and a CCR3 antagonist (SB328437, 5 ng/µl) was added to another part of the resultant mixture. The HUVECs were suspended in each medium at a concentration of $1 \times 10^3$ cells/ml, and seeded on matrigel (BD Biosciences, San Jose, Calif.) to be cultured. After 5 hours, the effect in angiogenesis promotion was observed using an inverted microscope (Leica, 6000B-4, Leica Microsystems GmbH, Wetzlar, Germany). Quantitative measurement was conducted, using Suite V3 software (Leica), on the length of a formed cord or tubular lumen.

Figure 21:
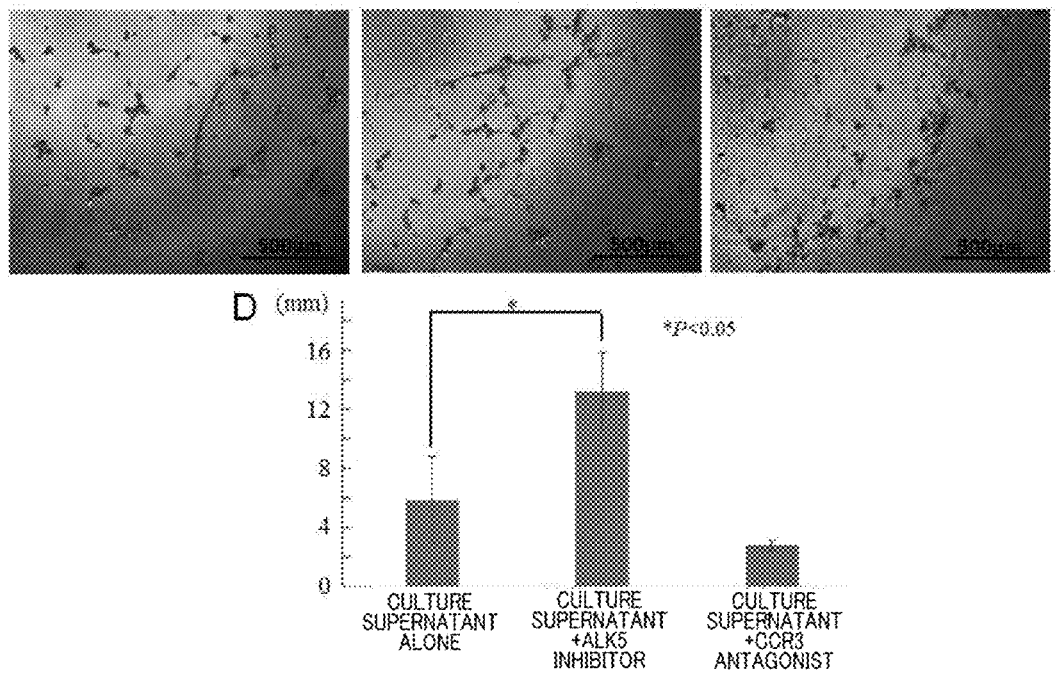
FIG. 21 includes photographs that show changes in in-vitro angiogenesis capacity in a case of human umbilical vain endothelial cells (HUVECs) cultured on matrigel, after having been suspended in mixture obtained by adding an ALK5 inhibitor (SB431542, 10 ng/µl) or a CCR3 antagonist (SB328437, 5 ng/µl) to culture supernatant of senescent dental pulp stem cells (DPSCs) of subcultured up to the 22nd passage. Photograph A is a phase-contrast microscope image of a control with the culture supernatant only. Photograph B is phase-contrast microscope image of a case of the culture supernatant to which the ALK5 inhibitor was added. Photograph C is a phase-contrast microscope image of a case of the culture conditioned medium to which the CCR3 antagonist was added. Graph D shows a statistical comparison of the lengths of new vessels. *P<0.05

The result shows that the culture supernatant of the senescent dental pulp stem cells, which contained the ALK5 inhibitor added thereto, promoted induction of angiogenesis (FIG. 21, Table 11).

TABLE 11

|  | DPSC CM + ALK5 Inhibitor 10 ng/µl | DPSC CM + CCR3 antagonist 5 ng/µl | DPSC CM |
|---|---|---|---|
| Length of New Blood Vessel | 13.2 ± 2.6 mm | 2.8 ± 0.3 mm | 5.9 ± 2.9 mm |

3. Changes in Neurite Outgrowth Caused by Addition of ALK5 Inhibitor and CCR3 Antagonist to Culture Conditioned Medium of Senescent Stem Cells of Human Dental Pulp The culture supernatant (5 µg/ml proteins) prepared in 1 above was added to TGW cells (human neuroblastoma cell line). Further, an ALK5 inhibitor (SB431542, 10 ng/µl) was added to a part of the resultant mixture, and a CCR3 antagonist (SB328437, 5 ng/µl) was added to another part of the resultant mixture. TGW cells to which only the culture supernatant was added was used as a negative control. TGW cells to which 50 ng/ml GDNF (Peproteck) was added was used as a positive control. Neurite outgrowth after 48 hours was observed and measured with an inverted microscope (Leica).

Figure 22:
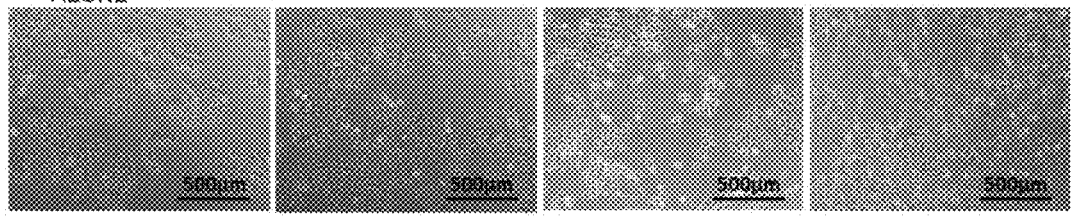
FIG. 22 includes photographs that show changes that were observed when neurite outgrowth was induced in vitro in TGW cells (human neuroblastoma cell line) by adding an ALK5 inhibitor (SB431542, 10 ng/µl) or a CCR3 antagonist (SB328437, 5 ng/µl) to culture conditioned medium of senescent dental pulp stem cells (DPSCs) subcultured up to the 22nd passage. Photograph A is a phase-contrast microscope image of a case of the culture supernatant alone. Photograph B is phase-contrast microscope image of a case of the culture supernatant to which the ALK5 inhibitor was added. Photograph C is a phase-contrast microscope image of a case of the culture supernatant to which the CCR3 antagonist was added. Photograph D is a phase-contrast microscope image of a positive control including GDNF added. Graph E shows a statistical comparison of lengths of neurites. *P<0.1, **P<0.05
Figure 22:
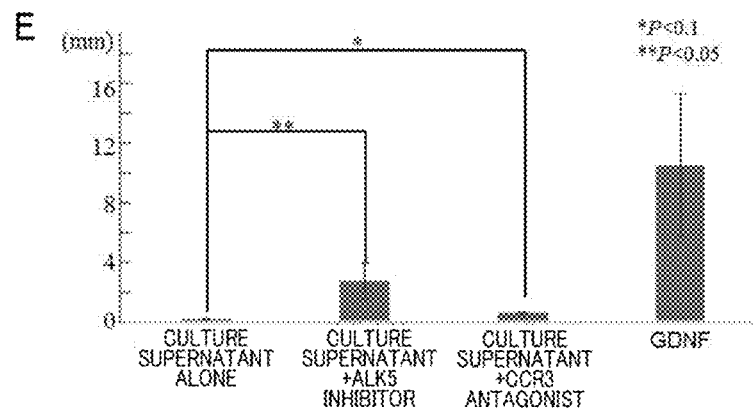

The result shows that the culture supernatant of the senescent dental pulp stem cells, which contained the ALK5 inhibitor or the CCR3 antagonist added thereto, significantly promoted neurite outgrowth (FIG. 22, Table 12).

TABLE 12

|  | DPSC CM | DPSC CM + ALK5 Inhibitor 10 ng/µl | DPSC CM + CCR3 antagonist 5 ng/µl | GDNF 50 ng/µl |
|---|---|---|---|---|
| Neurite Outgrowth Length | 111.5 ± 14.1 µm | 2710.5 ± 1223.0 µm | 518.7 ± 126.5 µm | 10540.1 ± 4800.7 µm |

4. Changes in Migration Promotion Caused by Addition of ALK5 Inhibitor and CCR3 Antagonist to Culture Supernatant of Senescent Stem Cells of Human Dental Pulp Fourth-passage human dental pulp cells were plated in DMEM containing 10% FBS in 10 cm dishes (FALCON) at $2 \times 10^4$ cells/ml. After 48 hours, the cells were detached, and a real-time horizontal chemotaxis analysis was performed using TAXIscan-FL (Effector Cell Institute, Tokyo) to measure the migratory capacity. Specifically, channels optimized (8 µm) for the size of the cells were formed between a silicon plate having 6 µm pores and a glass plate, and 1 µl of treated dental pulp cells ($10^5$ cells/ml) was injected to one end portion of each of the channels (n=4). As a control, one of the channels received nothing at the opposite end portion. Further, 1 µl of the culture supernatant (5 µg/ml protein) prepared in 1 above alone, 1 µl of the culture supernatant containing 1 µl of a 20 mg/ml ALK5 inhibitor (SB431542), and 1 µl of the culture supernatant containing 1 µl of a 20 mg/ml CCR3 antagonist (SB328437) were each placed in the opposite side portion of an associated one of the channel so as to form a constant concentration gradient. Based on the video images of migration, the number of migrating cells after 12 hours was measured.

Figure 23:
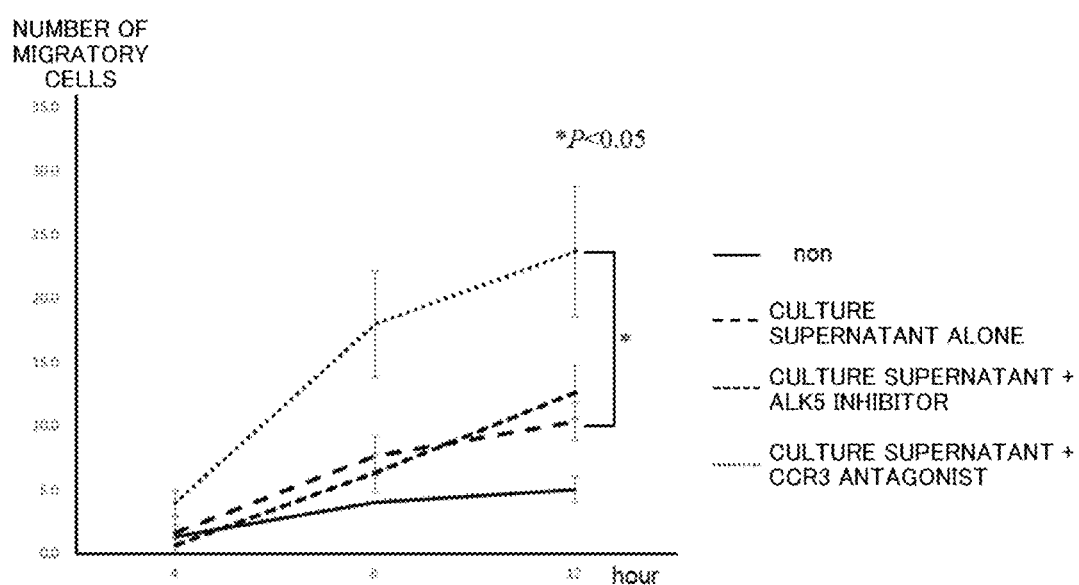
FIG. 23 shows changes in effect of promoting migratory capacity that occurred in vitro in fifth passage dental pulp cells when an ALK5 inhibitor (SB431542, 10 ng/µl) or a CCR3 antagonist (SB328437, 5 ng/µl) were added to culture conditioned medium of senescent dental pulp stem cells subcultured to the 22nd passage.

The result shows that addition of the CCR3 antagonist to G-CSF significantly enhanced the migratory capacity of dental pulp stem cell (FIG. 23, Table 13).

TABLE 13

|  | DPSC CM + ALK5 Inhibitor | DPSC CM + CCR3 antagonist | DPSC CM only | non |
| --- | --- | --- | --- | --- |
| Average ± SD | 12.7 ± 2.1 | 23.7 ± 5.1 | 10.3 ± 1.5 | 5.0 ± 1.0 |

INDUSTRIAL APPLICABILITY

The present invention is useful for dental tissue regeneration.

SEQUENCE LISTING FREE TEXT

SEQ ID NOS: 1 to 40: Primer

The invention claimed is:

1. A root canal filler comprising autologous or allogeneic dental pulp stem cells, an extracellular matrix, and a CCR3 antagonist.

\* \* \* \* \*